United States Patent [19]

Narita et al.

[11] Patent Number: 4,486,586
[45] Date of Patent: Dec. 4, 1984

[54] CEPHALOSPORIN DERIVATIVES

[75] Inventors: Yukio Narita, Yokohama; Seiji Iimura; Shimpei Aburaki, both of Tokyo; Jun Okumura, Yokohama; Takayuki Naito, Kawasaki, all of Japan

[73] Assignee: Bristol-Myers Company, New York, N.Y.

[21] Appl. No.: 465,374

[22] Filed: Feb. 10, 1983

[51] Int. Cl.³ ............... C07D 501/46; A61K 31/545
[52] U.S. Cl. ..................... 544/022; 544/25; 544/27; 544/21; 424/246
[58] Field of Search ............ 544/22, 25, 26, 27, 544/27; 424/246

[56] References Cited

U.S. PATENT DOCUMENTS 4,307,116  12/1981  Farge et al. ............... 424/246
4,307,233  12/1981  Farge et al. ............... 544/16

FOREIGN PATENT DOCUMENTS 0030630  6/1981  European Pat. Off. .
0053537  6/1982  European Pat. Off. .
0053074  6/1982  European Pat. Off. .
0053538  6/1982  European Pat. Off. .
1399086  5/1972  United Kingdom .

Primary Examiner—Nicholas S. Rizzo
Attorney, Agent, or Firm—Richard R. Lloyd

[57] ABSTRACT

7-{(Z)-2-(2-Aminothiazol-4-yl)-2-[(substituted)ox-yimino]acetamido}-3-[3-(quaternary ammonio)-1-propen-1-yl]-3-cephem-4-carboxylates and salts, esters and solvates thereof, having potent antibacterial activity, are provided. Processes for their preparation and intermediates in their preparation also are disclosed.

29 Claims, No Drawings

CEPHALOSPORIN DERIVATIVES

SUMMARY OF THE INVENTION

This application relates to novel cephalosporin derivatives of the formula

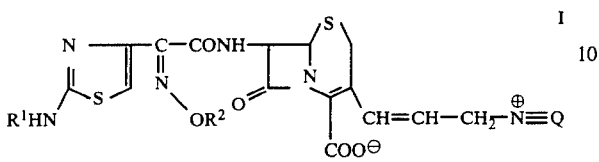

wherein $R^1$ is hydrogen or a conventional amino-protecting group, $R^2$ is hydrogen, a straight or branched chain alkyl group containing from 1 to 4 carbon atoms or a group of the formula

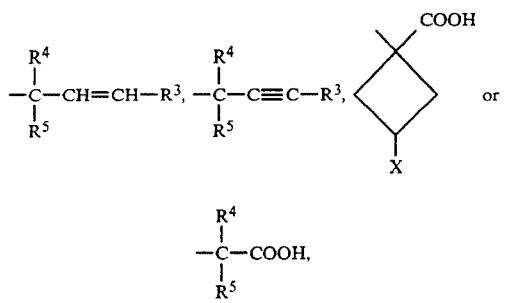

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, and to nontoxic pharmaceutically acceptable salts, physiologically hydrolyzable esters and solvates thereof.

In another aspect this invention relates to a process for the preparation of the compounds of Formula I and to intermediates in their preparation.

BACKGROUND AND PRIOR ART (A) Published European Patent Application No. 30,630 discloses a vast number of 7-acylamino-3-vinyl-cephalosporanic acid derivatives including, inter alia, those of the formula

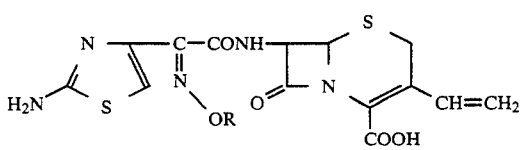

wherein R inter alia may be (lower)alkyl, (lower)alkenyl, (lower)alkynyl or carboxy(lower)alkyl. The compounds are prepared, inter alia, by reaction of the corresponding 3-halomethyl compound with a triarylphosphine, followed by treatment with a base and reaction with formaldehyde. In each case, the final 3-substituent is the vinyl group. There is no disclosure or suggestion of a quaternary ammonio-substituted propenyl moiety for the 3-substituent.

(B) U.K. Patent Specification No. 1,399,086 contains a generic disclosure encompassing a vast number of cephalosporins of the formula

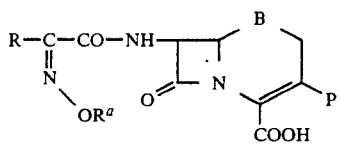

wherein R is hydrogen or an organic group, $R^a$ is an etherifying monovalent organic group linked to the oxygen through a carbon atom, B is $>S$ or $>S{\rightarrow}O$, and P is an organic group. In one embodiment, P may be inter alia a vinyl group of the formula

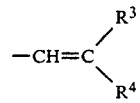

in which $R^3$ and $R^4$ independently may be hydrogen, nitrile, (lower)alkoxycarbonyl, or substituted or unsubstituted aliphatic, cycloaliphatic, araliphatic or aromatic. However, the 2-aminothiazol-4-yl group is not identified as a possible R substituent and there is no disclosure or suggestion that P may be a quaternary ammonio-substituted propenyl group. U.S. Pat. No. 3,971,778 and its divisionals U.S. Pat. Nos. 4,024,133, 4,024,137, 4,064,346, 4,033,950, 4,079,178, 4,091,209, 4,092,477 and 4,093,803 have similar disclosures.

(C) U.S. Pat. No. 4,307,233 discloses, inter alia, 3-vinyl cephalosporin derivatives of the formula

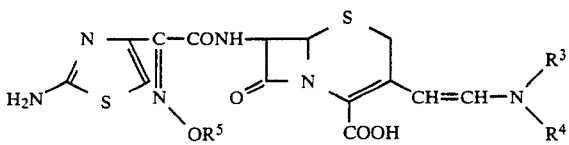

in which $R^5$ inter alia may be alkyl, vinyl, cyanomethyl or a protective group such as 2-methoxyprop-2-yl, and $R^3$ and $R^4$ are alkyl groups (optionally substituted by hydroxy, alkoxy, amino, alkylamino or dialkylamino) or phenyl groups, or $R^3$ and $R^4$, taken together with the nitrogen to which they are attached, may form a saturated heterocyclic ring of 5 or 6 members, optionally containing another hetero-atom selected from N, O and S, and optionally substituted by an alkyl group. The compounds are useful as intermediates in the preparation of 3-thiovinyl cephalosporin derivatives. There is no disclosure or suggestion of a quaternary ammonio-substituted propenyl moiety for the 3-substituent. Published United Kingdom Patent Application No. 2,051,062 is concordant thereto and has a similar disclosure.

(D) Published European Patent Application No. 53,537 discloses, inter alia, 3-vinylcephalosporin derivatives of the formula

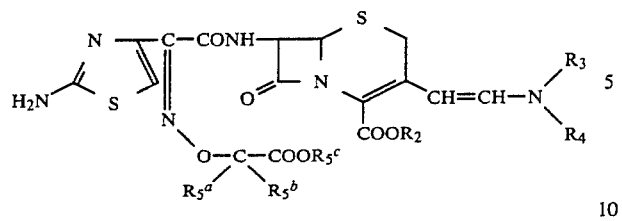

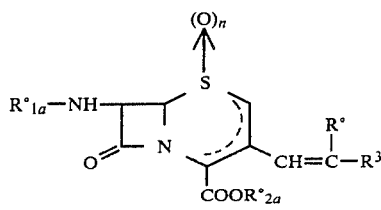

wherein R°$_{1a}$ (in one of several embodiments) may be

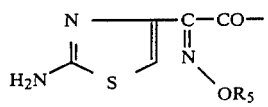

in which R$_5$ inter alia may be hydrogen, alkyl, vinyl, cyanomethyl, an oxime-protecting group such as trityl, etc., or a group of the formula

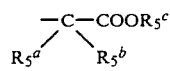

in which R$^a{}_5$ and R$^b{}_5$ are the same or different, and may be hydrogen, alkyl or, taken together, an alkylene radical of 2 or 3 carbon atoms, and R$^c{}_5$ is hydrogen or an acid-protecting radical; R°$_{2a}$ is hydrogen or an acid-protecting radical such as methoxy-methyl; R° (in one of several embodiments) may be a methyl group substituted by a 5- or 6-membered atomatic heterocyclic ring containing a single hetero atom, such as 2- or 3-pyridyl, or 2- or 3-thienyl or 2- or 3-furyl; and R$_3$ is a group of the formula

in which R$_4$ may be alkyl, trihalomethyl or optionally substituted phenyl.

These compounds are stated to be intermediates in the preparation of compounds in which the 3-substituent is a group of the formula

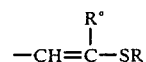

which are stated to have antibacterial activity.

Although this patent includes the possibility of R° being a methyl group substituted by an N-containing heterocyclic ring, in both the intermediates and final products (thus giving a heterocyclic-substituted propenyl moiety), it teaches only that the heterocyclic ring is attached via one of its carbon atoms. Thus, there is no suggestion of a quaternary ammonio-substituted propenyl group. The reference exemplifies R° in the intermediates and final products only as methyl. Further, in both the intermediates and final product, the propenyl group must contain a second substituent (—O$_3$SR$^4$ or —SR, respectively).

(G) Published European Patent Application No. 53,538 discloses, inter alia, 3-vinylcephalosporin intermediates of the formula in which R$_5{}^a$ and R$_5{}^b$ are the same or different and are hydrogen or alkyl, or taken together, form an alkylene group containing 2 or 3 carbon atoms, R$_5{}^c$ is an acid protecting group, R$_2$ is an acid protecting group such as an ester, R$_3$ and R$_4$ are the same or different and are hydrogen, alkyl (optionally substituted by hydroxy, alkoxy, amino, alkylamino or dialkylamino) or phenyl groups, or R$_3$ and R$_4$, taken together with the nitrogen to which they are attached, may form a saturated heterocyclic ring of 5 or 6 members, optionally containing another hetero-atom selected from N, O and S, and optionally substituted by an alkyl group. The compounds are useful as intermediates in the preparation of 3-thiovinyl cephalosporin derivatives. There is no disclosure or suggestion of a quaternary ammonio-substituted propenyl group for the 3-substituent.

(E) U.S. Pat. No. 4,307,116 discloses 3-thiovinylcephalosporins of the formula

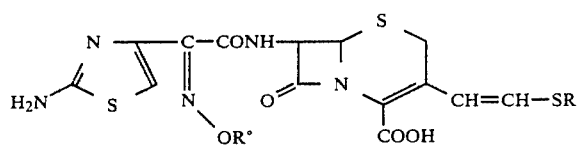

in which R° is hydrogen, alkyl, vinyl or cyanomethyl, and R inter alia may be one of a vast number of heterocyclic rings such as

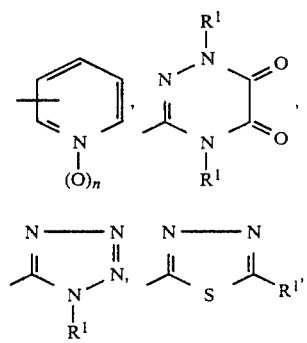

or the like. However, in each case, the heterocyclic ring is attached to the sulfur atom via a carbon atom of the heterocyclic ring. There is no disclosure or suggestion of a quaternary ammonio-substituted propenyl moiety for the 3-substituent. Although not formally related, published European Patent Application No. 53,961 has a similar disclosure, but includes 2-carboxyprop-2-yl, 1-carboxycyclobut-1-yl and the like as possible meanings of R°.

(F) Published European Patent Application No. 53,074 generically discloses a vast number of 3-vinylcephalosporin derivatives of the formula

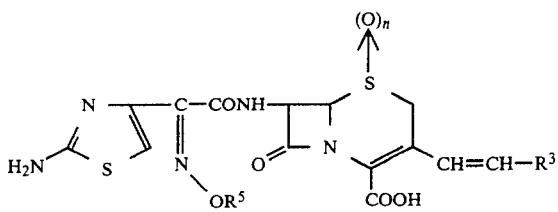

in which n is 0 or 1, $R^5$ is hydrogen, alkyl, vinyl, cyanomethyl or an oxime-protecting group, and $R^3$ is halogen.

COMPLETE DISCLOSURE

This application relates to novel cephalosporin derivatives which are potent antibacterial agents. More particularly, it relates to compounds of the formula

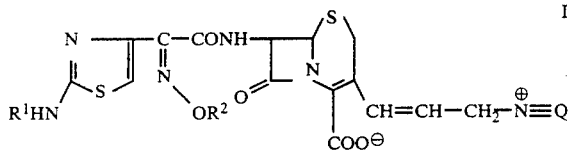

wherein $R^1$ is hydrogen or a conventional amino-protecting group, $R^2$ is hydrogen, a straight or branched chain alkyl group containing from 1 to 4 carbon atoms or a group of the formula

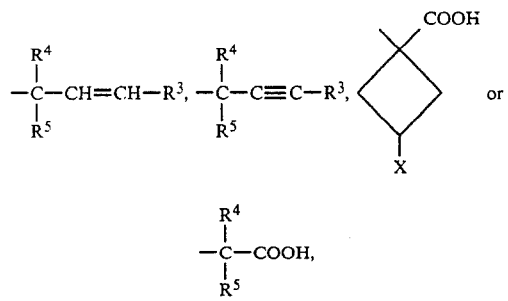

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, and nontoxic pharmaceutically acceptable salts and physiologically hydrolyzable esters thereof. Also included within the scope of the invention are the solvates (including hydrates) of the compounds of Formula I, as well as the tautomeric forms of the compounds of Formula I, e.g. the 2-iminothiazolin-4-yl form of the 2-aminothiazol-4-yl moiety.

In another aspect, this application relates to a process for the preparation of the compounds of Formula I and to certain 3-(3-halo-1-propen-1-yl)-substituted intermediates in their preparation.

As shown in the structural formula, the compounds of Formula I have the "syn" or "Z" configuration with respect to the alkoxyimino group. Because the compounds are geometric isomers, some of the "anti" isomer may also be present. This invention comprises compounds of Formula I containing at least 90% of the "syn" isomer. Preferably the compounds of Formula I are "syn" isomers which are essentially free of the corresponding "anti" isomers.

In addition to geometric isomers possible with respect to the alkoxyimino group, the compounds of Formula I (and the intermediates of Formulae IX and X) also form geometric (cis and trans) isomers about the double bond of the propenyl group. Both the cis ("Z") and trans ("E") isomers of these compounds are specifically included within the scope of this invention.

The nontoxic pharmaceutically acceptable salts of the compounds of Formula I include salts with mineral acids such as hydrochloric, hydrobromic, phosphoric and sulfuric, or with organic carboxylic acids or sulfonic acids such as acetic, trifluoroacetic, citric, maleic, oxalic, succinic, benzoic, tartaric, fumaric, mandelic, ascorbic, malic, methanesulfonic, p-toluenesulfonic and other acids known and used in the penicillin and cephalosporin arts. Preparation of these acid addition salts is carried out by conventional techniques.

Examples of physiologically hydrolyzable esters of the compounds of Formula I include indanyl, phthalidyl, methoxymethyl, acetoxymethyl, pivaloyloxymethyl, glycyloxymethyl, phenylglycyloxymethyl, and other physiologically hydrolyzable esters known and used in the penicillin and cephalosporin arts. Such esters are prepared by conventional techniques known in the art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsion in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage of the compounds of Formula I is dependent on such factors as the weight and age of the patient as well as the particular nature and severity of the disease, and is within the discretion of the physician. However, the dosage for adult human treatment will usually be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

The quaternary ammonio group of the formula

may be acyclic, cyclic, or a combination of the two, and may contain one or more additional hetero atoms selected from nitrogen, sulfur and oxygen.

An example of an acyclic quaternary ammonio group is a group of the formula

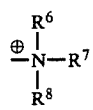

in which $R^6$, $R^7$ and $R^8$ may be the same or different and may, for example, be (lower)alkyl or substituted (lower)alkyl in which the substituents are, for example, halogen, amino with the provision that the amino group may not be on an α-carbon, hydroxy with the provision that the hydroxy group may not be on an α-carbon, (lower)alkoxy with the provision that the alkoxy group may not be on an α-carbon, (lower)alkylthio, (lower)alkylamino, di(lower)alkylamino, carbamoyl, (lower)alkenyl, phenyl(lower)alkyl, phenyl or substituted phenyl (in which the substituents may be, for example, halogen, hydroxy, amino, (lower)alkylamino, di(lower)alkylamino, acylamino, (lower)alkyl, (lower)alkylthio, (lower)alkoxy, or the like).

Examples of cyclic quaternary ammonio groups are fully unsaturated monocyclic heterocyclic ring systems, and bicyclic heterocyclic ring systems in which at least one N-containing ring is fully unsaturated. Suitable cyclic quaternary ammonio ring systems include, for example, those of the formulae

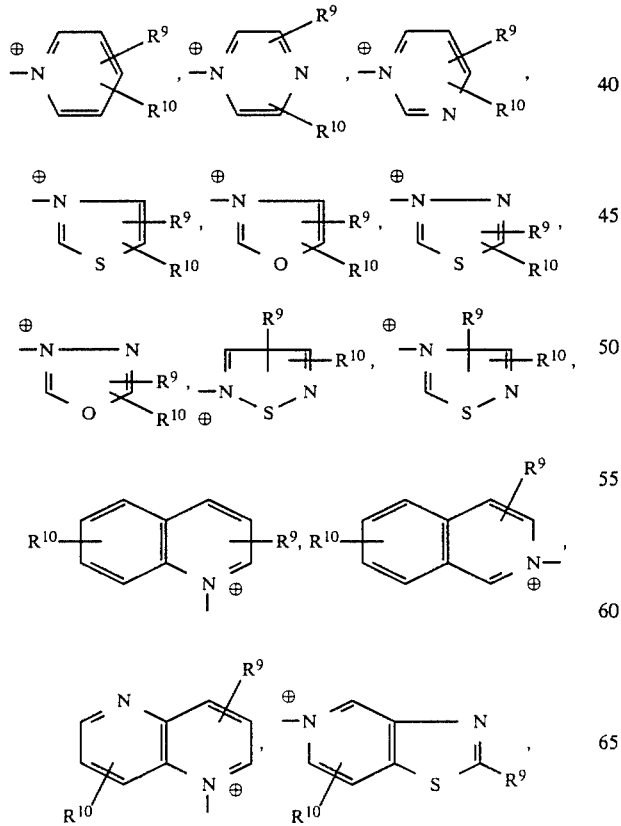

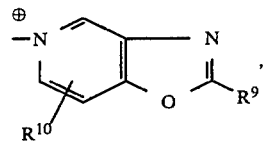

and the like, in which $R^9$ and $R^{10}$ are the same or different and may be, for example, hydrogen, halogen, amino, (lower)alkyl, (lower)alkenyl, (lower)alkylthio, hydroxy, (lower)alkoxy, (lower)alkoxy(lower)alkyl, halo(lower)alkyl, hydroxy(lower)alkyl, amino(lower)alkyl, (lower)alkylamino(lower)alkyl, di(lower)alkylamino(lower)alkyl, (lower)alkylamino, di(lower)alkylamino, carboxy(lower)alkyl, carboxy(lower)alkylamino, carbamoyl, acylamino, acyloxy, phenyl, pyridyl, amidino, guanidino and the like.

Examples of combined acyclic/cyclic quaternary ammonio groups include, for example, those of the formulae

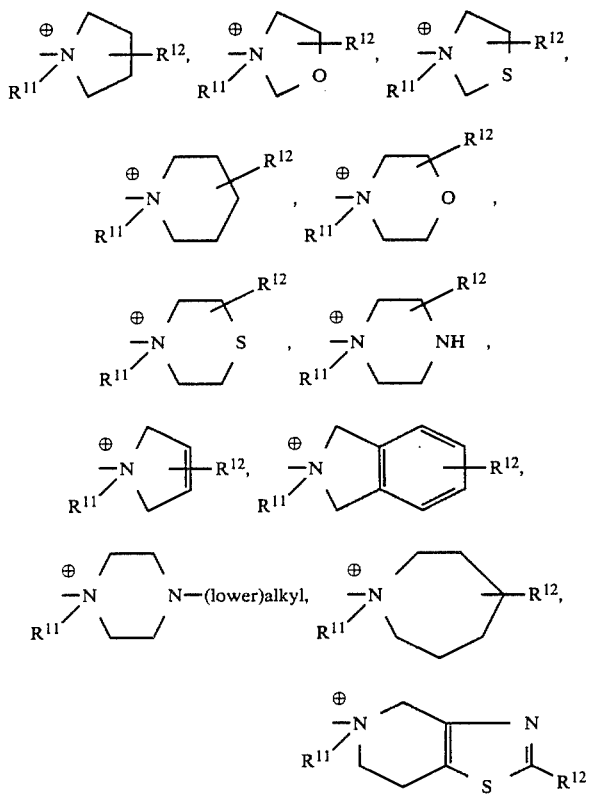

and the like, in which $R^{11}$ may be, for example, (lower)alkyl, (lower)alkoxy(lower)alkyl, hydroxy(lower)alkyl with the provision that the hydroxy may not be on an α-carbon, carboxy(lower)alkyl, amino(lower)alkyl with the provision that the amino may not be on an α-carbon, (lower)alkenyl, halo(lower)alkyl, allyl and the like, and $R^{12}$ may be, for example, hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino, guanidino and the like.

Preferred quaternary-ammonio groups are those of the formulae

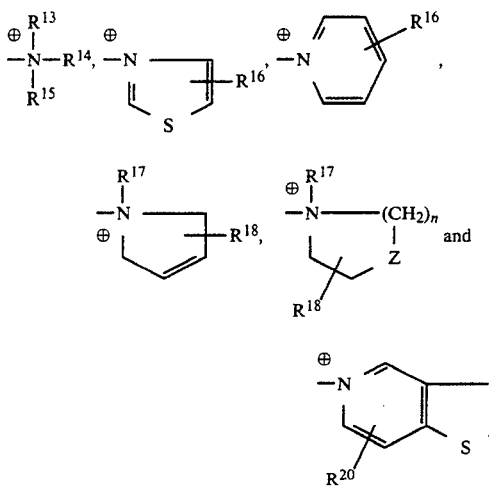

wherein $R^{13}$, $R^{14}$ and $R^{15}$ are the same or different and are (lower)alkyl, (lower)alkenyl, amino(lower)alkyl with the provision that the amino may not be on a α-carbon, or hydroxy(lower)alkyl with the provision that the hydroxy group may not be on an α-carbon;

$R^{16}$ is hydrogen, (lower)alkyl, (lower)alkoxy, (lower)alkylthio, amino, (lower)alkylamino, di(lower)alkylamino, formylamino, (lower)alkanoylamino, -hydroxy, hydroxy(lower)alkyl, halo(lower)alkyl, amino(lower)alkyl, (lower)alkoxy(lower)alkyl or carbamoyl;

$R^{17}$ is (lower)alkyl, (lower)alkoxy(lower)alkyl, halo(lower)alkyl, allyl, hydroxy(lower)alkyl with the provision that the hydroxy group is not on the α-carbon, amino(lower)alkyl with the provision that the amino group is not on the α-carbon, or phenyl(lower)alkyl;

$R^{18}$ is hydrogen, (lower)alkyl, (lower)alkoxy, (lower)alkoxy(lower)alkyl, (lower)alkylthio, amino, (lower)alkylamino, di(lower)alkylamino, hydroxy, hydroxy(lower)alkyl, amino(lower)alkyl, formylamino, (lower)alkanoylamino or carbamoyl;

n is an integer of from 1 to 3, inclusive;

Z is $CH_2$ or, when n is 2, Z also may be S, O or $N-R^{19}$, in which $R^{19}$ is hydrogen or (lower)alkyl; and $R^{20}$ and $R^{21}$ are the same or different and are hydrogen, (lower)alkyl, (lower)alkoxy, (lower)alkylthio, amino, (lower)alkylamino, di(lower)alkylamino, hydroxy, hydroxy(lower)alkyl, amino(lower)alkyl, (lower)alkoxy(lower)alkyl, carboxy(lower)alkyl, carboxy(lower)alkylamino, (lower)alkanoylamino, carboxy(lower)alkanoylamino or carbamoyl.

Particularly preferred quaternary ammonio groups are N-(lower)alkylpyrrolidinio (and especially N-methylpyrrolidinio), tri(lower)alkylammonio (and especially trimethylammonio), pyridinio, 2-methylthio-thiazolium and 2-methylthiazolio and 2-amino-5-thiazolo[4,5-c]pyridinio.

In the compounds of Formula I, particularly preferred values of $R^2$ are (lower)alkyl (and especially methyl), 1-carboxycycloalk-1-yl containing from 3 to 5 carbon atoms (and especially 1-carboxycyclobut-1-yl) and carboxy(lower)alkyl (and especially 2-carboxyprop-2-yl). The most preferred compounds of the invention are (1) 7-[(Z)-2-(2-aminothiazol-4-yl)-2-methoxyiminoacetamido]-3-[3-(1-methylpyrrolidinio)-1-propen-1-yl]-3-cephem-4-carboxylate, (2) 7-[(Z)-2-(2-aminothiazol-4-yl)-2-methoxyiminoacetamido]-3-(3-pyridinio-1-propen-1-yl)-3-cephem-4-carboxylate, (3) 7-[(Z)-2-(2-aminothiazol-4-yl)-2-(2-carboxy-2-propoxyimino)acetamido]-3-(3-pyridinio-1-propen-1-yl)-3-cephem-4-carboxylate, (4) 7-[(Z)-2-(2-aminothiazol-4-yl)-2-(1-carboxycyclobut-1-oxyimino)acetamido]-3-[3-(1-methylpyrrolidinio)-1-propen-1-yl]-3-cephem-4-carboxylate, (5) 7-[(Z)-2-(2-aminothiazol-4-yl)-2-(1-carboxycyclobut-1-oxyimino)acetamido]-3-(3-pyridinio-1-propen-1-yl)-3-cephem-4-carboxylate, (6) 7-[(Z)-2-(2-aminothiazol-4-yl)-2-(1-carboxycyclobut-1-oxyimino)acetamido]-3-[3-(2-amino-5-thiazolo[4,5-c]pyridinio)-1-propen-1-yl]-3-cephem-4-carboxylate, (7) 7-[(Z)-2-(2-aminothiazol-4-yl)-2-methoxyiminoacetamido]-3-[3-(trimethylammonio)-1-propen-1-yl]-3-cephem-4-carboxylate, (8) 7-[(Z)-2-(2-aminothiazol-4-yl)-2-methoxyiminoacetamido]-3-[3-(3-aminopyridinio)-1-propen-1-yl]-3-cephem-4-carboxylate, (9) 7-[(Z)-2-(2-aminothiazol-4-yl)-2-methoxyiminoacetamido]-3-[3-(1-methyl-3-pyrrolinio)-1-propen-1-yl]-3-cepehm-4-carboxylate,

(10) 7-[(Z)-2-(2-aminothiazol-4-yl)-2-(1-carboxycyclobut-1-oxyimino)acetamido]-3-[3-(1-methyl-3-pyrrolinio)-1-propen-1-yl]-3-cephem-4-carboxylate,

(11) 7-[(Z)-2-(2-aminothiazol-4-yl)-2-(2-carboxy-2-propoxyimino)acetamido]-3-[3-(1-methylpyrrolidinio)-1-propen-1-yl]-3-cephem-4-carboxylate,

(12) 7-[(Z)-2-(2-aminothiazol-4-yl)-2-(1-carboxycyclobut-1-oxyimino)acetamido]-3-[3-(2-methylthio-3-thiazolio)-1-propen-1-yl]-3-cephem-4-carboxylate,

(13) 7-[(Z)-2-(2-aminothiazol-4-yl)-2-methoxyiminoacetamido]-3-[3-(2-methyl-3-thiazolio)-1-propen-1-yl]-3-cephem-4-carboxylate,

(14) 7-[(Z)-2-(2-aminothiazol-4-yl)-2-(2-carboxy-2-propoxyimino)acetamido]-3-[3-(2-methylthio-3-thiazolio)-1-propen-1-yl]-3-cephem-4-carboxylate,

(15) 7-[(Z)-2-(2-aminothiazol-4-yl)-2-(1-carboxycyclobut-1-oxyimino)acetamido]-3-[3-(4-aminopyridinio)-1-propen-1-yl]-3-cephem-4-carboxylate,

(16) 7-[(Z)-2-(2-aminothiazol-4-yl)-2-methoxyiminoacetamido]-3-[3-(4-amino-1-pyridinio)-1-propen-1-yl]-3-cephem-4-carboxylate,

(17) 7-[(Z)-2-(2-aminothiazol-4-yl)-2-methoxyiminoacetamido]-3-[3-(2-methylthio-3-thiazolio)-1-propen-1-yl]-3-cephem-4-carboxylate,

(18) 7-[(Z)-2-(2-aminothiazol-4-yl)-2-(1-carboxycyclobut-1-oxyimino)acetamido]-3-[3-(3-amino-1-pyridinio)-1-propen-1-yl]-3-cephem-4-carboxylate,

(19) 7-[(Z)-2-(2-aminothiazol-4-yl)-2-methoxyiminoacetamido]-3-[3-(4-carbamoyl-1-pyridinio)-1-propen-1-yl]-3-cephem-4-carboxylate,

(20) 7-[(Z)-2-(2-aminothiazol-4-yl)-2-methoxyiminoacetamido]-3-[3-(2-amino-5-thiazolo[4,5-c]pyridinio)-1-propen-1-yl]-3-cephem-4-carboxylate and

(21) 7-[(Z)-2-(2-aminothiazol-4-yl)-2-(1-carboxycyclobut-1-oxyimino)acetamido]-3-[3-(2-methyl-3-thiazolio)-1-propen-1-yl]-3-cephem-4-carboxylate.

The numbering system utilized herein for the various reactants, intermediates and final products is as follows:

[Roman Numeral] − [Arabic Numeral (if appropriate)] [Letter (if appropriate)].

The Roman Numeral designates whether the compound is a final product [I] or an intermediate or other reactant [all other Roman Numerals]. The Arabic Numerals and Letters are not used in those instances where the overall class (genus) of compounds is meant.

The Arabic Numeral designates the particular meaning of substituent $R^2$, and the assigned meanings may be seen, for example, in Preparation No. 1. If the particular $R^2$ group contains a carboxyl group which is protected by a conventional carboxyl-protecting group, a "prime" (') is used after the Arabic Numeral to indicate this fact. No "prime" is used if the carboxyl group is unprotected. A "prime" also is used with the generic $R^2$ substituent (i.e. $R^{2'}$) when generically referring to an $R^2$ group containing a protected carboxyl group.

The Letter at the end of the compound number refers to the particular meaning of the quaternary ammonio group

For convenience, the Arabic Numerals and Letters assigned to some of the preferred $R^2$ groups and quaternary ammonio groups are set forth below.

| Arabic Numeral | $R^2$ |
|---|---|
| 1 | = methyl |
| 2 | = ethyl |
| 3 | = allyl |
| 4 | = 2-carboxyprop-2-yl |
| 5 | = 1-carboxycyclobut-1-yl |
| 6 | = 1-carboxy-3-chlorocyclobut-1-yl |
| 7 | = 2-propyn-1-yl |

| Letter | $\oplus{-}N{\equiv}Q$ |
|---|---|
| A | = 1-methylpyrrolidinio |
| B | = pyridinio |
| C | = 2-amino-5-thiazolo[4,5-c]pyridinio |
| D | = trimethylammonio |
| E | = 3-aminopyridinio |
| F | = 1-methyl-3-pyrrolinio |
| G | = 2-(methylthio)thiazolio |
| H | = 2-methylthiazolio |
| I | = 4-aminopyridinio |
| J | = 4-carbamoylpyridinio |

In the primary evaluation of the compounds of this invention, the Minimum Inhibitory Concentrations (MIC's) of the compounds were determined by the two-fold serial agar dilution method in Mueller-Hinton agar against 32 strains of test organisms in six groups. The geometric means of the MIC's determined in these tests are shown in Table 1.

TABLE 1

| Compound Number | Geometric Mean of MIC (mcg/ml) | | | | | |
|---|---|---|---|---|---|---|
| | (G+)-Ia (5) | (G+)-Ib (5) | (G−)-Ia (5) | (G−)-Ib (5) | (G−)-II (5) | (G−)-III (7) |
| I-1B | 0.20 | 0.52 | 0.012 | 0.050 | 0.10 | 5.7 |
| I-4B | 6.0 | 15 | 0.046 | 0.37 | 0.41 | 5.0 |
| I-1A | 0.22 | 0.59 | 0.021 | 0.11 | 0.13 | 5.1 |
| I-5B | 1.6 | 4.7 | 0.019 | 0.23 | 0.17 | 2.0 |
| I-5A | 1.8 | 4.7 | 0.038 | 0.23 | 0.26 | 2.6 |
| I-5C | 1.3 | 4.4 | 0.015 | 0.15 | 0.14 | 2.7 |

TABLE 1-continued

| Compound Number | Geometric Mean of MIC (mcg/ml) | | | | | |
|---|---|---|---|---|---|---|
| | (G+)-Ia (5) | (G+)-Ib (5) | (G−)-Ia (5) | (G−)-Ib (5) | (G−)-II (5) | (G−)-III (7) |
| I-1E | 0.10 | 0.30 | <0.0053 | 0.050 | 0.043 | 5.7 |
| I-1F | 0.15 | 0.39 | 0.014 | 0.074 | 0.10 | 3.1 |
| I-5F | 1.5 | 4.0 | 0.037 | 0.22 | 0.17 | 2.4 |
| I-4A | 2.3 | 4.1 | 0.036 | 0.20 | 0.17 | 2.3 |
| I-1D | 0.17 | 0.59 | 0.0093 | 0.074 | 0.10 | 3.1 |
| I-5G | 0.84 | 2.8 | 0.014 | 0.13 | 0.13 | 1.9 |
| I-1H | 0.10 | 0.30 | 0.0093 | 0.050 | 0.074 | 5.7 |
| I-4G | 1.8 | 5.4 | 0.021 | 0.22 | 0.20 | 3.5 |
| I-5I | 1.6 | 4.7 | 0.019 | 0.20 | 0.22 | 3.5 |
| I-1I | 0.11 | 0.34 | <0.016 | 0.10 | 0.15 | >25 |
| I-1G | 0.15 | 0.39 | 0.014 | 0.074 | 0.085 | 7.6 |
| I-5E | 1.2 | 3.1 | 0.016 | 0.15 | 0.15 | 1.9 |
| I-1J | 0.26 | 0.61 | 0.016 | 0.11 | 0.13 | 5.7 |

(G+)-Ia: Penicillin-sensitive *S. aureus* (5 strains)
(G+)-Ib: Penicillin-resistant *S. aureus* (5 strains)
(G−)-Ia: Cephalothin-sensitive *E. coli* (2 strains), *Kl. pneumoniae* (1 strain) and *Pr. mirabilis* (2 strains)
(G−)-Ib: Cephalothin-resistant *E. coli* (3 strains) and *Kl. pneumoniae* (3 strains)
(G−)-II: *M. morganii* (1 strain), *Ent. cloacae* (2 strains) and *Ser. marcescens* (2 strains)
(G−)-III: *Ps. aeruginosa* (7 strains)

In another aspect, this invention relates to processes for the preparation of the compounds of Formula I. The preferred procedure is shown below in Reaction Scheme 1, while alternative procedures are shown in Reaction Schemes 2, 3 and 4. In the reaction schemes, m may be 0 or 1. The abbreviation "Tr" represents the trityl (triphenylmethyl) group, which is a preferred amino-protecting group. The abbreviation "Ph" represents the phenyl group. Thus, the —CH(Ph)$_2$ moiety is the benzhydryl group, which is a preferred carboxyl-protecting group. When $R^2$ contains a carboxyl group, it is desirable to protect the carboxyl group with a conventional carboxyl-protecting group such as the t-butyl moiety.

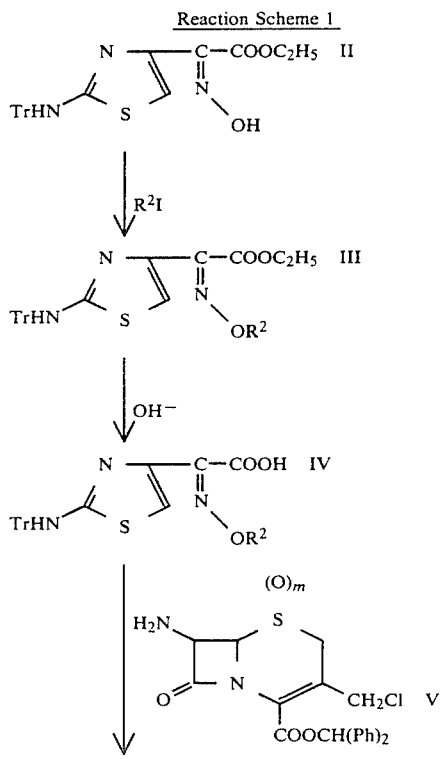

Reaction Scheme 1

-continued
Reaction Scheme 1

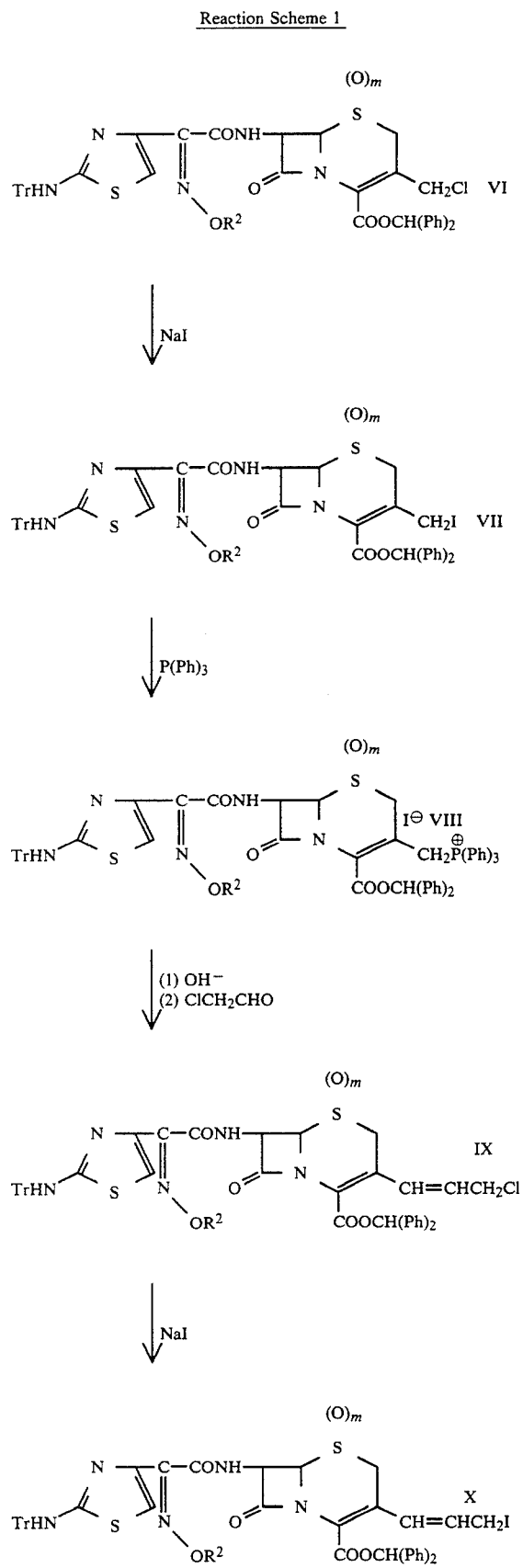

-continued
Reaction Scheme 1

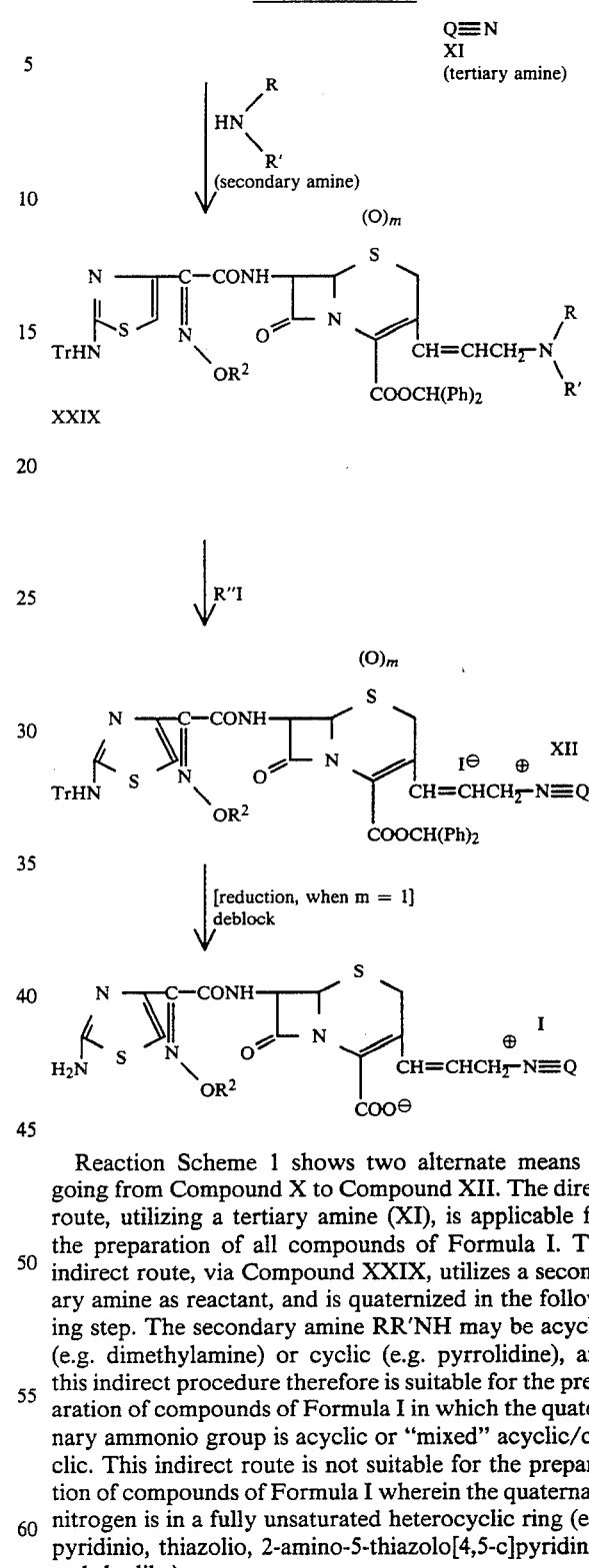

Reaction Scheme 1 shows two alternate means of going from Compound X to Compound XII. The direct route, utilizing a tertiary amine (XI), is applicable for the preparation of all compounds of Formula I. The indirect route, via Compound XXIX, utilizes a secondary amine as reactant, and is quaternized in the following step. The secondary amine RR'NH may be acyclic (e.g. dimethylamine) or cyclic (e.g. pyrrolidine), and this indirect procedure therefore is suitable for the preparation of compounds of Formula I in which the quaternary ammonio group is acyclic or "mixed" acyclic/cyclic. This indirect route is not suitable for the preparation of compounds of Formula I wherein the quaternary nitrogen is in a fully unsaturated heterocyclic ring (e.g. pyridinio, thiazolio, 2-amino-5-thiazolo[4,5-c]pyridinio, and the like).

Alternate Reaction Scheme 2, shown below, also utilizes a tertiary amine as a reactant, and therefore is suitable for the preparation of all compounds of Formula I. Alternate Reaction Scheme 3, on the other hand, utilizes a secondary amine as a reactant, which is quaternized in the final step. Accordingly, like the indirect step of Reaction Scheme 1 (via Compound XXIX), Reaction Scheme 3 is suitable for the preparation of compounds of Formula I where the quaternary ammonio group is acyclic or mixed acyclic/cyclic, but not those compounds wherein the quaternary nitrogen is in a fully unsaturated heterocyclic ring.

Reaction Scheme 4, shown below, is a shortened version of Reaction Scheme 1, in that two steps are eliminated. That is, the direct route of Reaction Scheme 4 goes directly from Compound VIII to Compound XII (rather than VIII→IX→X→XII in the direct route of Reaction Scheme 1), while the indirect route of Reaction Scheme 4 is two steps from Compound VIII to Compound XII (VIII→XXX→XII) rather than four steps in the indirect route of Reaction Scheme 1 (VIII→IX→X→XXIX→XII). As discussed above, the direct route of Reaction Scheme 4 is suitable for the preparation of all compounds of Formula I, while the indirect route is suitable for the preparation of the compounds of Formula I in which the quaternary ammonio group is acyclic or mixed acyclic/cyclic.

Intermediates of Formula XXI (3-formylcephalosporin derivatives) are known compounds or may be prepared by known procedures. See, for example, U.S. Pat. Nos. 3,351,596, 4,166,115, 4,279,818 and 4,331,664 which teach the preparation of 3-formylceph-3-em compounds by oxidation of the corresponding 3-hydroxymethylceph-3-em compounds.

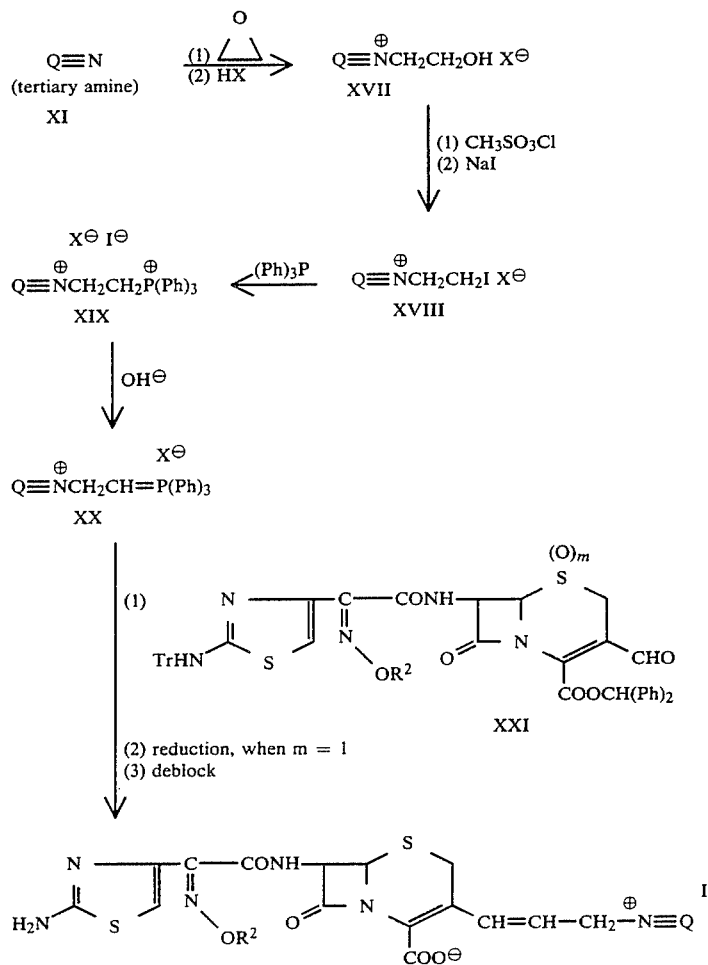

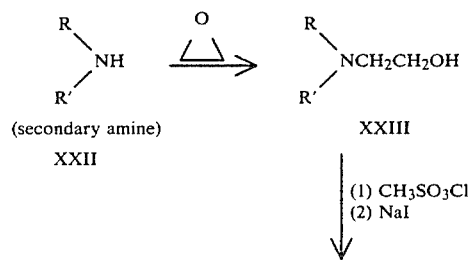

Reaction Scheme 3
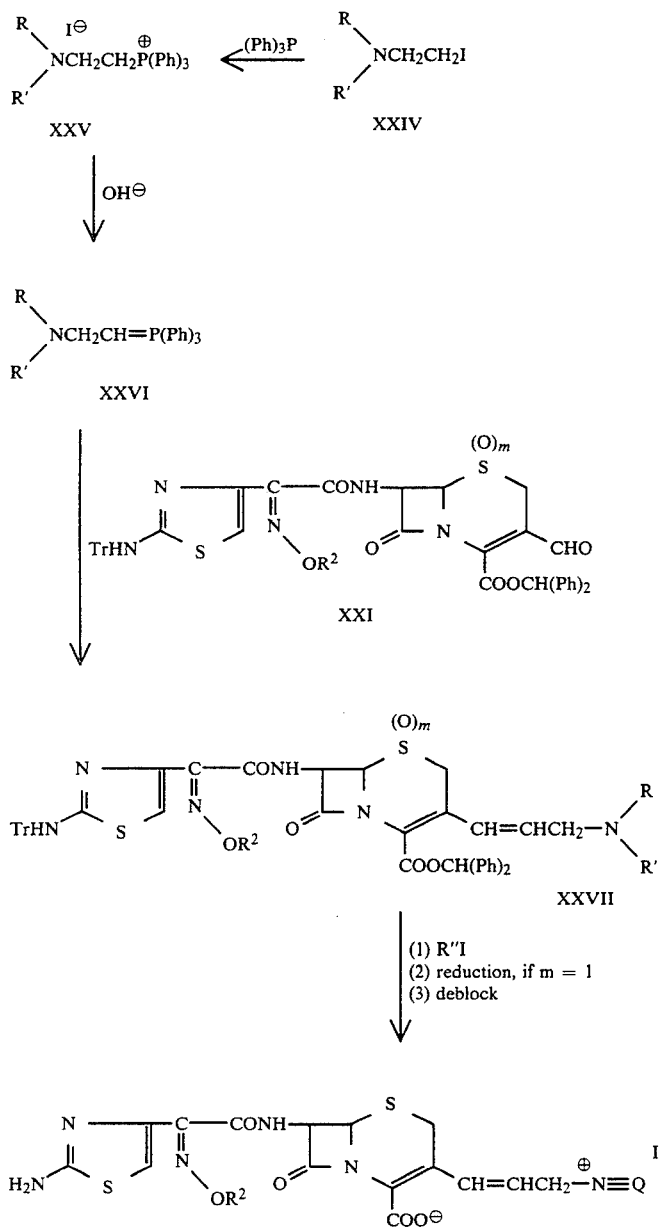
Reaction Scheme 4
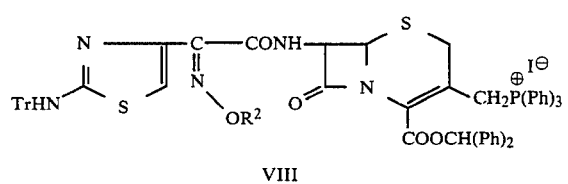

Reaction Scheme 4 -continued

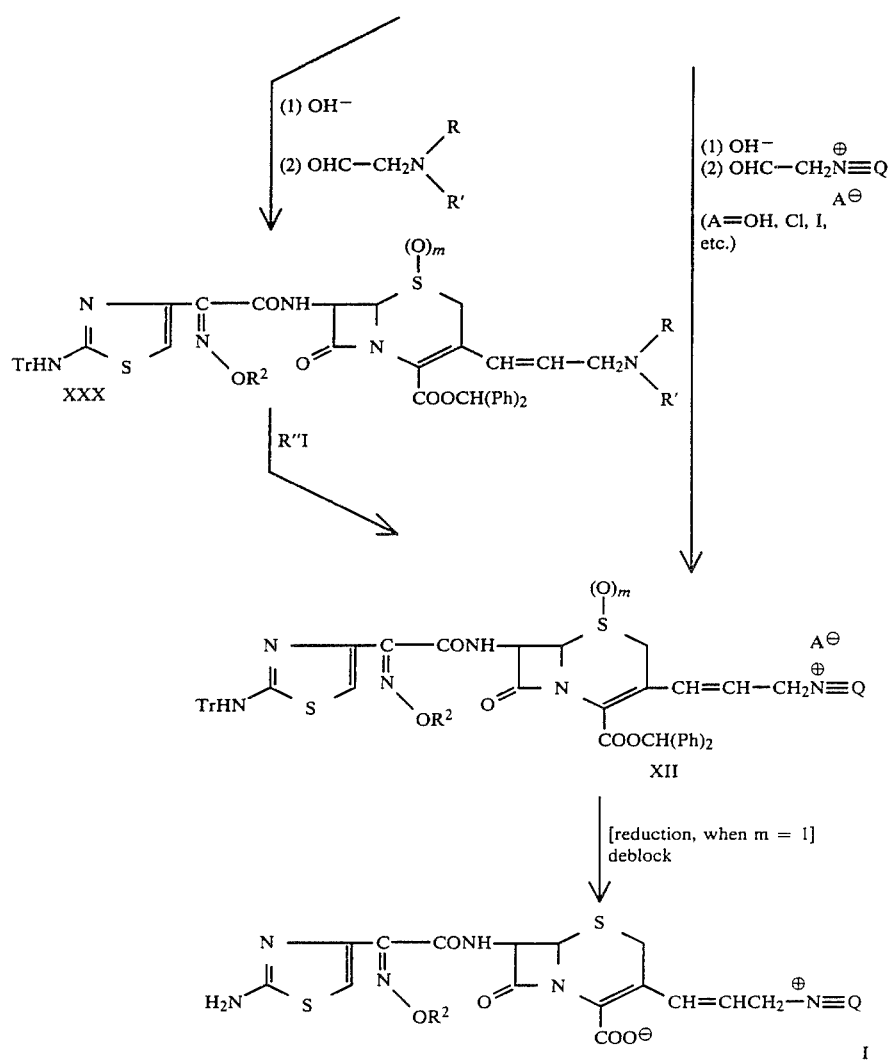

Although Reaction Scheme 1, above, shows a preferred multi-step procedure for the preparation of the compounds of Formula I, it will be appreciated that other starting materials and procedures may be utilized to prepare the intermediates used in the key step. Thus, the key step in Reaction Scheme 1 is the reaction of Compound X with the tertiary amine of XI to produce the "protected" product XII (or the indirect reaction of Compound X with a secondary amine, followed by quaternization to produce product XII). Compound X may, of course, be prepared by various other procedures.

The present invention provides a process for the preparation of compounds of the formula

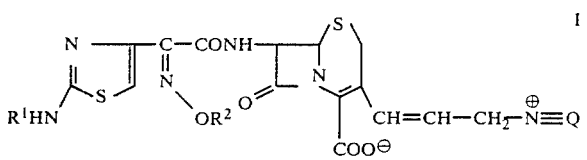

wherein $R^1$ is hydrogen or a conventional amino-protecting group, $R^2$ is hydrogen, a straight or branched chain alkyl group containing from 1 to 4 carbon atoms, or a group of the formula

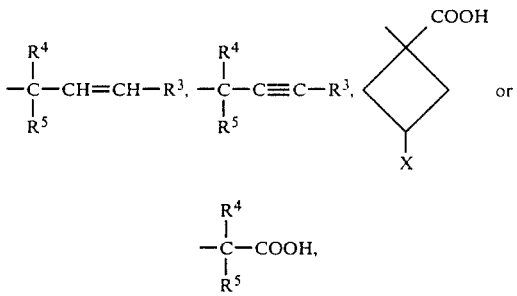

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonium group, and nontoxic pharmaceutically acceptable salts, physiologically hydrolyzable esters and solvates thereof, which process comprises reacting a compound of the formula

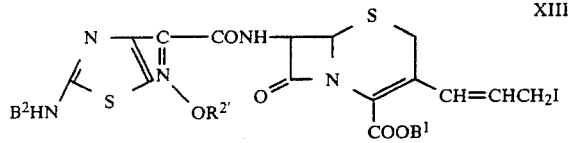

XIII wherein R²′ is the same as R² or is a group of the formula

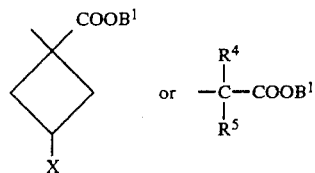

in which X, R⁴ and R⁵ are as defined above, B¹ is a conventional carboxyl-protecting group, B² is a conventional amino-protecting group and m is 0 or 1, with a tertiary amine, to produce a compound of the formula

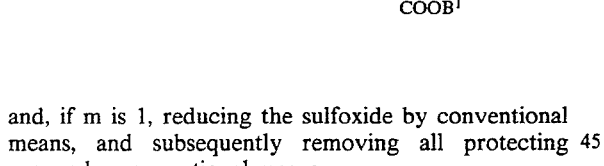

XIV and, if m is 1, reducing the sulfoxide by conventional means, and subsequently removing all protecting groups by conventional means.

The present invention also provides a process for the preparation of compounds of the formula

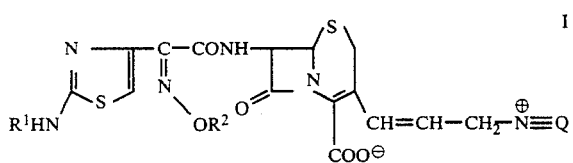

I wherein R¹ is hydrogen or a conventional amino-protecting group, R² is hydrogen, a straight or branched chain alkyl group containing from 1 to 4 carbon atoms, or a group of the formula

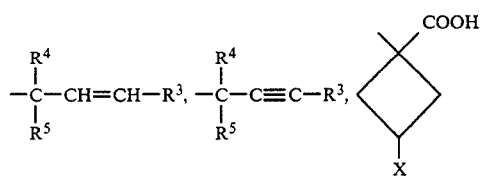

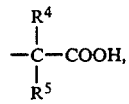

in which R³ is hydrogen, (lower)alkyl or carboxyl, X is halogen, hydroxy or (lower)alkoxy, and R⁴ and R⁵ are each independently hydrogen, methyl or ethyl, or R⁴ and R⁵, taken together with the carbon atom to which they are attached, may be a cycloalkylidene ring containing from 3 to 5 carbon atoms, and

is a quaternary ammonio group, and nontoxic pharmaceutically acceptable salts, physiologically hydrolyzable esters and solvates thereof, which process comprises reacting a compound of the formula

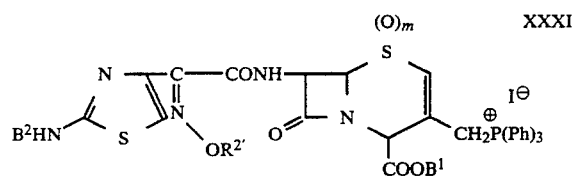

XXXI wherein R²′ is the same as R² or is a group of the formula

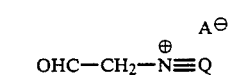

in which X, R⁴ and R⁵ are as described above, B¹ is a conventional carboxyl-protecting group, B² is a conventional amino-protecting group and m is 0 or 1, with an appropriate base such as hydroxyl ion and then with a compound of the formula $$OHC-CH_2-\overset{\oplus}{N}\equiv Q \quad A^{\ominus}$$

in which

is a quaternary ammonio group and A⁻ is hydroxyl, chloro, bromo or iodo, to produce a compound of the formula

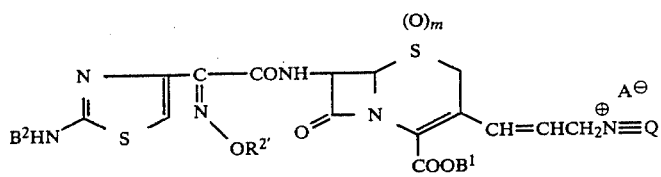

XXXII and, if m is 1, reducing the sulfoxide by conventional means, and subsequently removing all protecting groups by conventional means.

The present invention also provides a process for the preparation of compounds of the formula

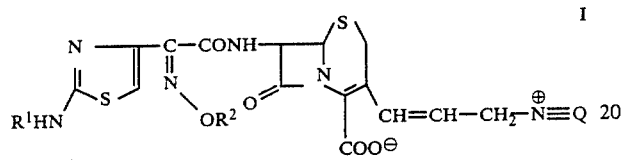

wherein $R^1$ is hydrogen or a conventional amino-protecting group, $R^2$ is hydrogen, a straight or branched chain alkyl group containing from 1 to 4 carbon atoms, or a group of the formula

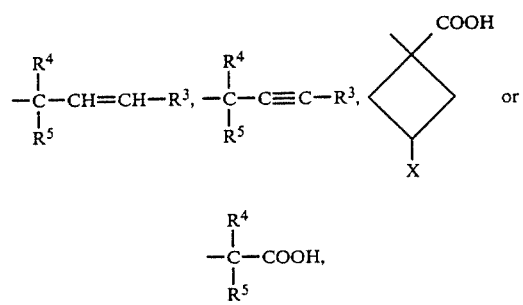

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonium group, and nontoxic pharmaceutically acceptable salts, physiologically hydrolyzable esters and solvates thereof, which process comprises reacting a compound of the formula

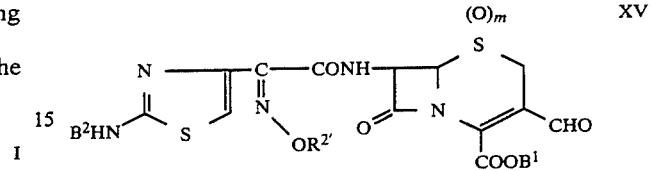

wherein $R^{2'}$ is the same as $R^2$ or is a group of the formula

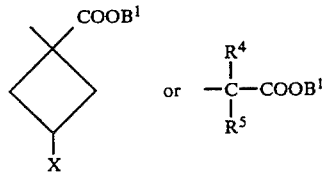

in which X, $R^4$ and $R^5$ are as defined above, $B^1$ is a conventional carboxyl-protecting group. $B^2$ is a conventional amino-protecting group and m is 0 or 1, with a compound of the formula $$(C_6H_5)_3P=CHCH_2\overset{\oplus}{N}\equiv Q \ X^{\ominus} \qquad XX$$

in which X is chloro, bromo or iodo, to produce a compound of the formula

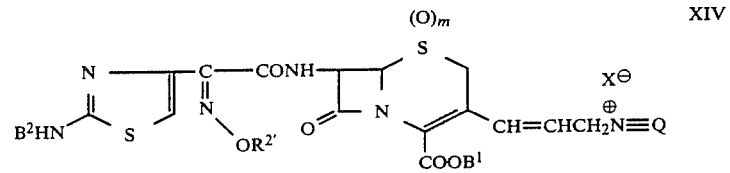

XIV and, if m is 1, reducing the sulfoxide by conventional means, and subsequently removing all protecting groups by conventional means.

The reactions are carried out in a non-aqueous organic solvent such as dimethyl sulfoxide, hexamethylphosphoramide, methylene chloride, chloroform, ethyl ether, hexane, ethyl acetate, tetrahydrofuran, acetonitrile and the like, or mixtures of such solvents. The reactions are conveniently carried out at a temperature of from about $-10°$ C. to about $+50°$ C.; we normally prefer to conduct the reactions at room temperature. In Reaction Scheme 1, at least one mole of the tertiary amine (or secondary amine) should be used per mole of Compound X; we normally prefer to utilize from about 25% to 100% excess of the tertiary amine. Similarly, at least one mole of Compound R"I should be used per mole of Compound XXIX.

Carboxyl-protecting groups suitable for use as $B^1$ in the above reactions are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as $B^2$ are also well-known in the art, and include the trityl group and acyl groups such as chloroacetyl, formyl and trichloroethoxycarbonyl. Amino-protecting groups which are readily removed by treatment with acid, e.g. the trityl group, are preferred.

In Reaction Scheme 1, 2, 3, or 4, when the cephalosporin nucleus is utilized in the form of the 1-oxide (m=1), the 1-oxide is prepared by known procedures such as oxidation with m-chloroperbenzoic acid, peracetic acid, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

As used herein, the terms acylamino and acyloxy refer to an acylated amino or acylated hydroxy group in which the acyl moiety is (lower)alkanoyl (e.g. formyl, acetyl, propionyl, butyryl, isobutyryl, isovaleryl, etc.), aroyl (e.g. benzoyl, etc.), (lower)alkanesulfonyl (e.g. mesyl, ethanesulfonyl, etc.) or arylsulfonyl (e.g. benzenesulfonyl, tosyl, etc.).

As used herein, the terms "(lower)alkyl", "(lower)alkoxy", "(lower)alkylthio" (or the like) mean straight or branched chain alkyl, alkoxy, alkylthio (or the like) groups containing from 1 to 6 carbon atoms, inclusive.

In another embodiment, this invention relates to novel intermediates of the formula

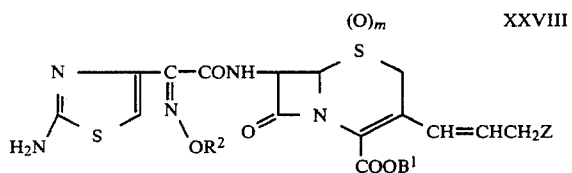

wherein Z is chloro, bromo or iodo, m is 0 or 1 and $R^2$ is hydrogen, a straight or branched chain alkyl group containing from 1 to 4 carbon atoms, or a group of the formula

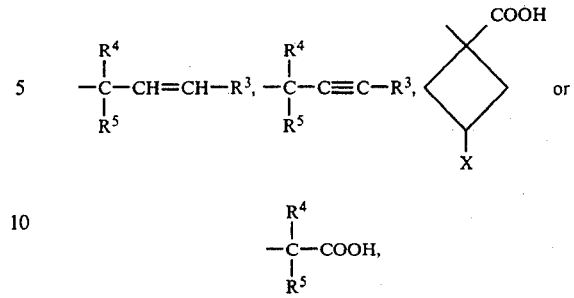

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and salts and esters thereof. Also included are compounds of Formula XXVIII in which the amino and/or carboxyl groups are protected by conventional amino-protecting or carboxyl-protecting groups.

Preparation No. 1

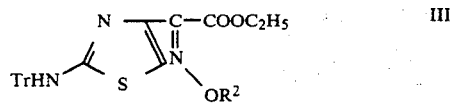

Ethyl (Z)-2-Methoxyimino-2-(2-tritylaminothiazol-4-yl)acetate (III-1)

A mixture of ethyl (Z)-2-hydroxyimino-2-(2-tritylaminothiazol-4-yl) acetate (II) (5.00 g, 10.9 mmoles), CH₃I (2.04 mL, 32.8 mmoles) and K₂CO₃ (4.54 g, 32.8 mmoles) in dry dimethylsulfoxide (DMSO) (100 mL) was stirred at room temperature overnight and then poured into water (250 mL). The precipitate which formed was collected by filtration, washed with water and dried to give the title compound (5.15 g, quantitative yield). Mp. 115° C. (dec.).

NMR: $\delta^{CDCl_3}$ ppm 1.32 (3H, t), 3.98 (3H, s), 4.30 (2H, q), 6.42 (1H, s), 7.2 (1H, s), 7.25 (15H, s).

Compounds III-2, III-3, III-4', III-5', III-6' and III-7 were prepared by the general procedure set forth above, but replacing the methyl iodide with the appropriate iodide or bromide.

| Compound | $R^2$ (or $R^{2'}$) | Yield (%) | Mp (°C.) | Literature Mp (°C.) |
|---|---|---|---|---|
| III-1 | methyl | 100 | 115 (dec.) | 120 (dec.)[1] |
| III-2 | ethyl | 67 | 97-98 | * |
| III-3 | allyl | * | * | * |
| III-4' | —C(CH₃)₂COOtButyl | 100 | 125-126 | 123.5-125[2]; 134[3] |
| III-5' |  COOtButyl | 68 | 81-83 | not reported[3] |

-continued

| Compound | R² (or R²') | Yield (%) | Mp (°C.) | Literature Mp (°C.) |
|---|---|---|---|---|
| III-6' | COOtBuyl / Cl (diamond structure) | 36 | 75–85 | (new compound) |
| III-7 | —CH₂C≡CH | 94 | 70–73 | not reported[4] |

*The ester was hydrolyzed without isolation
[1] Tetrahedron, 34, 2233 (1978)
[2] U.S. Pat. No. 4,258,041
[3] U.S. Pat. No. 4,288,434
[4] U.S. Pat. No. 4,294,960

Preparation No. 2

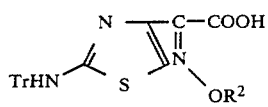

(Z)-2-Methoxyimino-2-(2-tritylaminothiazol-4-yl)acetic acid (IV-1)

The ethyl ester III-1 prepared in Preparation No. 1 (6.00 g, 12.7 mmoles) in ethanol (120 mL) was treated with 2N NaOH (12.7 mL) at room temperature overnight. The reaction mixture was adjusted to pH 8 by the addition of powdered dry ice and the solvent was evaporated under reduced pressure. The residue was dissolved in water (100 mL) and the solution was acidified with 1N HCl to pH 2 and then extracted with ethyl acetate (3×50 mL). The combined extracts were washed with a saturated aqueous NaCl solution, dried and evaporated. The residue was crystallized from ethyl acetate-hexane to afford 5.56 g (yield 98%) of the title product. Mp. 138°–143° C. (dec.).

NMR: $\delta^{CDCl_3}$ ppm 3.89 (3H, s), 6.52 (1H, s), 7.2 (15H, s).

Compounds IV-2, IV-3, IV-4', IV-5', IV-6' and IV-7 were prepared by the general procedure set forth above.

| Compound | R² (or R²') | Yield (%) | Mp (°C., dec.) | Literature Mp (°C., dec.) |
|---|---|---|---|---|
| IV-1 | methyl | 98 | 138–143 | ca. 140[1] |
| IV-2 | ethyl | 85 | 140–145 | not reported[1] |
| IV-3 | allyl | 66 | 170–178 | ca. 170[1] |
| IV-4' | —C(CH₃)₂COOtBuyl | 77 | 174–175 | 152–156[2]; 190[3] |
| IV-5' | COOtBuyl (diamond structure) | 78 | 163–164 | not reported[3] |
| IV-6' | COOtBuyl / Cl (diamond structure) | 51 | 125–135 | new compound |
| IV-7 | —CH₂C≡CH | 88 | 136–138 | [4] |

[1] Tetrahedron, 34, 2233 (1978)
[2] U.S. Pat. No. 4,258,041
[3] U.S. Pat. No. 4,288,434
[4] The corresponding NH₂ compound is described in U.S. Pat. No. 4,294,960

Preparation No. 3

Benzhydryl 3-Hydroxymethyl-7-phenylacetamido-3-cephem-4-carboxylate

To a stirred suspension of phosphate buffer (pH 7, 162.5 ml) and wheat bran (20 g, dry) at room temperature was added 7-phenylacetamidocephalosporanic acid sodium salt (5 g, 12.1 mmoles) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 mL) followed by a 0.5M solution of diphenyldiazomethane in methylene chloride (24 mL). The pH was then adjusted to 3.0 with 28% phosphoric acid. After 1 hour the reaction mixture was allowed to rise to 20° C. Heptane (56 mL) was slowly added and the resulting crystalline title product was recovered by filtration. Yield of the title product was 3.0 g (50%).

Preparation No. 4

Benzhydryl 7-Amino-3-chloromethyl-3-cephem-4-carboxylate (V)

To a slurry of PCl₅ (8.3 g, 40 mmoles) in CH₂Cl₂ (100 mL) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 mL) and the mixture was allowed to stand at −20° C. for 16 hours and then at room temperature for 20 minutes with stirring. The resulting solution was washed with ice-water (2×20 mL) and saturated aqueous NaCl (10 mL), dried over MgSO₄ and concentrated in vacuo. The gummy residue (12 g) was dissolved in a mixture of CHCl₃ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm$^{-1}$.
UV: $\lambda_{max}{}^{EtOH}$ 265 nm (E₁ cm$^{1\%}$ 160).
NMR: $\delta_{ppm}{}^{DMSO-d6+CDCl3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

Preparation No. 5

Benzhydryl 3-Chloromethyl-7-[(Z)-2-methoxyimino-2-(2-tritylaminothiazol-4-yl)acetamido]-3-cephem-4-carboxylate (VI-1)

Benzhydryl 7-amino-3-chloromethyl-3-cephem-4-carboxylate prepared in Preparation No. 4 (2.29 g, 5.52 mmoles) in CH₃CN (57 mL) was treated with bis(trimethylsilyl)acetamide (BSA, 4.09 mL, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IV-1) (2.04 g, 4.60 mmoles) and PCl₅ (1.15 g, 5.52 mmoles) in methylene chloride (20 mL). The mixture was stirred at room temperature for 30 minutes, poured into cold water (200 mL) and extracted with ethyl acetate (3×100 mL). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VI-1 as an amorphous powder.

NMR: $\delta^{CDCl3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

Preparation No. 6

Benzhydryl 3-Iodomethyl-7-[(Z)-2-methoxyimino-2-(2-tritylaminothiazol-4-yl)acetamido]-3-cephem-4-carboxylate (VII-1)

A mixture of the 3-chloromethyl derivative prepared in Preparation No. 5 (VI-1) (1.50 g, 1.79 mmoles) and NaI (1.34 g, 8.93 mmoles) in methyl ethyl ketone (30 mL) was stirred at room temperature for 1 hour. After evaporation of the solvent the residue was dissolved in ethyl acetate (100 mL) and washed with water, aqueous Na₂S₂O₃ and aqueous NaCl, dried and evaporated to give the title compound VII-1 (1.47 g, 89%) as an amorphous powder.

NMR: $\delta^{CDCl3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

Preparation No. 7

Benzhydryl 3-Chloromethyl-7-[(Z)-2-ethoxyimino-2-(2-tritylaminothiazol-4-yl)acetamido]-3-cephem-4-carboxylate (VI-2)

To a solution of (Z)-2-ethoxyimino-2-(2-tritylaminothiazol-4-yl)acetic acid (IV-2) (1.095 g, 2.4 mmoles) in dichloromethane (20 mL) was added phosphorous pentachloride (500 mg). After stirring for 1 hour at room temperature, the mixture was added in one portion to an ice-cooled solution of Compound V (1.083 g, 2.4 mmoles) and BSA (1 mL) in dichloromethane (20 mL). After stirring for 0.5 hour the reaction mixture was poured into 10% aqueous NaHCO₃ (200 mL) and extracted with CHCl₃ (100 mL). The extract was washed with water, dried over MgSO₄, and evaporated under reduced pressure. The residue was chromatographed on a silica gel column. Elution with CHCl₃ gave VI-2 as an amorphous powder, 1.76 g (86%).

NMR: $\delta^{CDCl3}$ ppm 1.40 (3H, t, CH₂CH₂), 3.53 (2H, ABq, 2-H), 4.37 (2H, s, —CH₂Cl), 4.60 (2H, q, —CH₂CH₃), 4.90 (1H, d, 6-H), 5.89 (1H, d, 7-H), 6.88 (1H, s, thiazole-H), 6.91 (1H, s, benzhydryl-CH).

Preparation No. 8

Diphenylmethyl 7-[(Z)-2-Ethoxyimino-2-(2-tritylaminothiazol-4-yl)acetamido]-3-iodomethyl-3-cephem-4-carboxylate (VII-2)

A mixture of VI-2 prepared in Preparation No. 7 (1.07 g, 1.25 mmoles) and NaI (562 mg, 2.75 mmoles) in acetone (20 mL) was stirred for 1 hour. The mixture was filtered and the filtrate was poured into water and extracted with ethyl acetate. The organic layer was washed successively with 5% aqueous Na₂S₂O₃, water and saturated aqueous NaCl, dried over MgSO₄ and evaporated to give 1.04 g (89%) of Compound VII-2.

NMR: $\delta^{CDCl3}$ ppm 3.55 (2H, q, 2-H), 4.27 (2H, s, CH₂I), 5.02 (1H, d, 6-H), 5.87 (1H, d, 7-H), 6.68 (1H, s, thiazole ring H), 6.93 (1H, s, benzhydryl-CH).

Preparation No. 9

Benzhydryl 7-[(Z)-2-Allyloxyimino-2-(2-tritylaminothiazol-4-yl)acetamido]-3-chloromethyl-3-cephem-4-carboxylate (VI-3)

To a suspension of Compound V (1.35 g, 3 mmoles) in methylene chloride (20 mL) was added BSA (1.1 mL, 4.5 mmoles), and the mixture was stirred for 30 minutes at room temperature to become a clear solution. A mixture of (Z)-2-allyloxyimino-2-(2-tritylaminothiazol-4-yl)acetic acid (IV-3) (1.40 g, 3.0 mmoles) and phosphorous pentachloride (690 mg, 3.3 mmoles) in methylene chloride (20 mL) was stirred for 15 minutes at room temperature and poured in one portion into the solution of the trimethylsilylated Compound V. The mixture was stirred for 20 minutes at room temperature and diluted with ethyl acetate (200 mL), washed with aqueous sodium bicarbonate and water, dried and evaporated under reduced pressure. The oily residue was purified by silica gel column chromatography (Wakogel, C-200, 30 g). The column was eluted with chloroform and the fractions containing the desired product were combined. Evaporation under reduced pressure afforded the title compound (VI-3) as an amorphous powder, yield 2.32 g (89%). Mp. 100°–115° C. (dec.).

IR: $\nu_{max}{}^{KBr}$ cm$^{-1}$ 3390, 1790, 1730, 1680, 1530, 1380, 1250, 1160, 1020.
NMR: $\delta^{CDCl3}$ ppm 3.50 (2H, 2-H), 4.32 (2H, s, 3-CH₂), 4.6–6.1 (7H, m, CH₂CH=CH₂ and 6,7-H), 6.70 (1H, s, thiazole-H), 6.90 (1H, s, Ph₂CH), 7.1–7.6 (30H, m, phenyl protons).

Anal. Calc'd. for C₄₈H₄₀N₅O₅S₂Cl.1/3CHCl₃: C, 64.05; H, 4.45; N, 7.73; S, 7.08; Cl, 7.82. Found: C, 64.13; 63.99; H, 4.61, 4.64; N, 7.50, 7.30; S, 6.85, 6.85; Cl, 7.55, 7.46.

Preparation No. 10

Benzhydryl 7-[(Z)-2-Allyloxyimino-2-(2-tritylaminothiazol-4-yl)acetamido]-3-iodomethyl-3-cephem-4-carboxylate (VII-3)

A mixture of Compound VI-3 (2.30 g, 2.65 mmoles) and sodium iodide (2 g, 13.3 mmoles) in acetone (15 mL) was stirred for 1 hour at room temperature and then evaporated under reduced pressure. A solution of the oily residue in ethyl acetate (200 mL) was washed with 10% sodium thiosulfate and water, evaporated under reduced pressure to afford Compound VII-3 as an amorphous powder, which was used in the subsequent step without further purification. Yield 2.52 g (99%).

Preparation No. 11

Benzhydryl 3-Chloromethyl-7-[(Z)-2-(2-t-butoxycarbonylprop-2-oxyimino)-2-(2-tritylaminothiazol-4-yl)acetamido]-3-cephem-4-carboxylate (VI-4')

Procedure 1

A mixture of (Z)-2-(2-t-butoxycarbonylprop-2-oxyimino)-2-(2-tritylaminothiazol-4-yl)acetic acid (IV-4') (1.94 g, 3.6 mmoles) DCC (742 mg, 3.6 mmoles) and N-hydroxybenztriazole (486 mg, 3.6 mmoles) in tetrahydrofuran (THF) (45 mL) was stirred at room temperature for 45 minutes, during which dicyclohexylurea separated. The dicyclohexylurea was removed by filtration and the filtrate was mixed with V (1.5 g, 3.6 mmoles). The mixture was stirred overnight at room temperature and then evaporated in vacuo. The residual oil was dissolved in $CHCl_3$ (20 mL), washed with saturated aqueous $NaHCO_3$ and saturated aqueous NaCl, dried over $MgSO_4$ and evaporated to dryness. The residue (3.9 g) was dissolved in n-hexane:$CHCl_3$ (1:2) and passed through a silica gel column (40 g) using the same solvent system. Fractions containing the title compound were evaporated in vacuo to give 1.3 g (39%) of VI-4' melting at >100° C. (dec.).

IR: $\nu_{max}^{KBr}$ cm$^{-1}$ 3390, 1790, 1715, 1690.

UV: $\lambda_{max}^{EtOH}$ nm 240 ($E_1~_{cm}^{1\%}$ 280), 265 ($E_1~_{cm}^{1\%}$ 190).

NMR: $\delta^{CDCl_3}$ ppm 1.45 (9H, s), 1.63 & 1.66 (6H, each s), 3.49 (2H, broad s), 4.34 (2H, s), 4.96 (1H, d, J=4.5 Hz), 5.90 (1H, d-d, J=4.5 & 7.5), 6.66 (1H, s), 6.86 (1H, s), 7.0–7.5 (25H, m), 8.23 (1H, d, J=7.5 Hz).

Procedure 2

A solution of V (1.86 g, 4.49 mmoles) in $CH_3CN$ (46.5 mL) was treated with BSA (3.33 mL, 13.5 mmoles) at room temperature for 50 minutes to give a clear solution. To the solution was added an acid chloride solution which had been prepared from IV-4' (2.56 g, 4.49 mmoles) and $PCl_5$ (1.12 g, 5.38 mmoles) in methylene chloride (26 mL). The mixture was stirred at room temperature for 30 minutes, poured into cold water (100 mL) and extracted with ethyl acetate (3×50 mL). The combined extracts were washed with aqueous NaCl, dried and evaporated. The residual syrup (5 g) was chromatographed on a silica gel (100 g) column by eluting with 10:1 mixture of toluene and ethyl acetate. The fractions containing the desired compound were combined and evaporated to afford 2.84 g (65%) of VI-4'.

Preparation No. 12

Benzhydryl 7-[(Z)-2-(2-t-Butoxycarbonylprop-2-oxyimino)-2-(2-tritylaminothiazol-4-yl)acetamido]-3-iodomethyl-3-cephem-4-carboxylate (VII-4')

A mixture of VI-4' (500 mg, 0.53 mmole) and NaI (240 mg, 1.6 mmoles) in acetone (3 mL) was stirred for 2 hours at room temperature and then evaporated in vacuo. To the residue were added $CH_2Cl_2$ (20 mL) and water (10 mL). The organic layer was washed with 10% w/v sodium thiosulfate (5 mL) and aqueous NaCl (5 mL), dried over $MgSO_4$ and evaporated to dryness to give 540 mg (99%) of VII-4' as an amorphous powder melting at 106° C. (dec.).

IR: $\nu_{max}^{KBr}$ cm$^{-1}$ 3350, 1790, 1690.

UV: $\lambda_{max}^{EtOH}$ nm 240 ($E_1~_{cm}^{1\%}$ 270), 265 ($E_1~_{cm}^{1\%}$ 190).

NMR: $\delta^{CDCl_3}$ ppm 1.44 (9H, s), 1.65 (6H, s), 3.54 (2H, ABq), 4.28 (2H, s), 4.98 (1H, d, J=4.5 Hz), 5.85 (1H, d-d, J=4.5 & 7.5 Hz), 6.70 (1H, s), 6.90 (1H, s), 7.1–7.5 (25H, m).

Preparation No. 13

Diphenylmethyl 7-[(Z)-2-(1-t-Butoxycarbonylcyclobut-1-oxyimino)-2-(2-tritylaminothiazol-4-yl)acetamido]-3-chloromethyl-3-cephem-4-carboxylate (VI-5')

Phosphorus pentachloride (1.46 g, 7 mmoles) was added to a suspension of (Z)-2-(1-t-butoxycarbonylcyclobut-1-oxyimino)-2-(2-tritylaminothiazol-4-yl)acetic acid [IV-5'] (4.09 g, 7 mmoles) in 70 mL of dry methylene chloride, and the mixture was stirred for 1 hour at room temperature. The acid chloride solution was added at −20° C. to a solution of silylated 7-ACA ester, which was prepared by adding BSA (5.6 mL, 21 mmoles) to a stirred suspension of benzhydryl 7-amino-3-chloromethyl-3-cephem-4-carboxylate hydrochloride [V] (3.16 g, 7 mmoles) in dry methylene chloride (70 mL). The mixture was stirred for 20 minutes at −10° C. and then at room temperature for 40 minutes. The reaction mixture was evaporated and diluted with ethyl acetate (300 mL), and the organic layer was washed with 5% aqueous sodium bicarbonate, water and a saturated sodium chloride solution. After drying over sodium sulfate, the solvent was evaporated and the residue was purified by silica gel column chromatography (Wako gel C-200, 60 g); elution with chloroform. The fractions containing the desired product were combined and evaporated to obtain 5.88 g (86%) of VI-5' as a yellow powder.

IR: $\nu_{max}^{KBr}$ cm$^{-1}$ 1790, 1725, 1690, 1525.

UV: $\lambda_{max}^{EtOH}$ nm 240 ($E_1~_{cm}^{1\%}$=232), 265 ($E_1~_{cm}^{1\%}$=181).

Preparation No. 14

Diphenylmethyl 7-[(Z)-2-(1-t-Butoxycarbonylcyclobut-1-oxyimino)-2-(2-tritylaminothiazol-4-yl)acetamido]-3-iodomethyl-3-cephem-4-carboxylate (VII-5')

To a stirred solution of VI-5' (5.4 g, 5.5 mmoles) in acetone (108 mL) was added sodium iodide (2.48 g, 16.5 mmoles), and the mixture was stirred at room temperature for 3 hours. The reaction mixture was then filtered and evaporated to dryness, and the residue was dissolved in ethyl acetate (200 mL). The solution was washed with water (100 mL), 10% w/v sodium thiosulfate (40 mL) and saturated sodium chloride (3×70 mL). After drying over magnesium sulfate, the solvent was removed under reduced pressure to give 5.38 g (91%) of VII-5' as a yellow powder.

IR: $\nu_{max}^{KBr}$ cm$^{-1}$ 1790, 1725, 1690, 1525.

UV: $\lambda_{max}^{EtOH}$ nm 240 (E$_1$ $_{cm}$$^{1\%}$=197), 265 (E$_1$ $_{cm}$$^{1\%}$=154).

NMR: $\delta^{CDCl3}$ ppm 1.45 (9H, s), 1.8–2.8 (6H, m), 3.52 (2H, ABq), 4.25 (2H, s), 4.98 (1H, d, J=5.3 Hz), 5.87 (1H, dd, J=9 & 5.3 Hz), 6.70 (1H, s), 6.88 (1H, s), 6.90 (1H, s), 7.28 (25H, s), 8.41 (1H, d, J=9 Hz).

Preparation No. 15

Diphenylmethyl 3-chloromethyl-7-[(Z)-2-propargyloxyimino-2-(2-tritylaminothiazol-4-yl)acetamido]-3-cephem-4-carboxylate [VI-7]

Phosphorus pentachloride (910 mg) was added to a solution of (Z)-2-propargyloxyimino-2-(2-tritylaminothiazol-4-yl)acetic acid (IV-7) (1.7 g, 3.6 mmoles) in dichloromethane (30 mL). After stirring for 1 hour at room temperature the mixture was added in one portion to an ice-cooled solution of (V) (1.98 g, 4.4 mmoles) and N,O-bis(trimethylsilyl)acetamide (1.5 mL) in dichloromethane (30 mL). After stirring for 1 hour, the reaction mixture was poured into 10% aqueous NaHCO$_3$ (300 mL) and extracted with ethyl acetate (300 mL). The extract was washed with water, dried over MgSO$_4$ and evaporated under reduced pressure. The residue was chromatographed on a silica gel column. Elution with CHCl$_3$ gave the title compound [VI-7] as an amorphous powder weighing 2.1 g (66%).

NMR: $\delta^{CDCl3}$ ppm 2.45 (1H, t, CH), 3.53 (2H, d, 2-CH$_2$), 4.37 (2H, s, —CH$_2$Cl), 4.83 (2H, d, O—CH$_2$C≡CH), 5.03 (1H, d, 6-H), 5.90 (1H, q, 7-H), 6.70 (1H, s, thiazole-H), 6.92 (1H, s, benzhydryl-CH).

Preparation No. 16

Diphenylmethyl 7-[(Z)-2-propargyloxyimino-2-(2-tritylaminothiazol-4-yl)acetamido]-3-iodomethyl-3-cephem-4-carboxylate [VII-7]

A mixture of diphenylmethyl 3-chloromethyl-7-[(Z)-2-propargyloxyimino-2-(2-tritylaminothiazol-4-yl)acetamido]-3-cephem-4-carboxylate (VI-7) (2.0 g, 2.3 mmoles) and NaI (1.04 g, 6.9 mmoles) in acetone (40 mL) was stirred for 1 hour. The mixture was filtered and the filtrate was poured into water and extracted with ethyl acetate. The organic layer was washed with 5% aqueous Na$_2$S$_2$O$_3$, water and a saturated aqueous NaCl, successively. It was then dried over MgSO$_4$ and evaporated to give 2.2 g (98%) of the title compound [VII-7].

NMR: $\delta^{CDCL3}$ ppm 2.45 (1H, t, CH), 3.53 (2H, d, 2-CH$_2$), 4.25 (2H, s, CH$_2$I), 4.83 (2H, d, O—CH$_2$), 5.0 (1H, d, 6-H), 5.80 (1H, q, 7-H), 6.70 (1H, s, thiazole-H), 6.92 (1H, s, benzhydryl-CH).

Preparation No. 17

Diphenylmethyl 7-[(Z)-2-Methoxyimino-2-(2-tritylaminothiazol-4-yl)acetamido]-3-triphenylphosphoniomethyl-3-cephem-4-carboxylate Iodide (VIII-1)

A mixture of diphenylmethyl 7-[(Z)-2-(2-tritylaminothiazol-4-yl)-2-methoxyiminoacetamido]-3-iodomethyl-3-cephem-4-carboxylate (VII-1, 7.8 g, 8.4 mmoles) and triphenylphosphine (4.4 g, 16.8 mmoles) in benzene (160 ml) was stirred at room temperature for 1 hour. The resulting precipitate was collected by filtration to afford 8.0 g of the title compound VIII-1. The mother liquor was concentrated and the residue was triturated with n-hexane to yield an additional amount (1.3 g) of VIII-1. Total yield 9.3 g (93%).

IR: $\nu_{max}^{KBr}$ cm$^{-1}$ 1770, 1700, 1660, 1510.

Preparation No. 18

Diphenylmethyl 3-(3-Chloro-1-propen-1-yl)-7-[(Z)-2-methoxyimino-2-(2-tritylaminothiazol-4-yl)acetamido]-3-cephem-4-carboxylate (IX-1)

The phosphonium iodide VIII-1 (20 g, 17 mmoles) in chloroform (130 ml) was shaken with aqueous sodium hydroxide (10 ml 2N NaOH plus 70 ml water) and the chloroform layer was washed with water and dried over sodium sulfate. To the chloroform solution was added chloroacetaldehyde (2 g, 25 mmoles) and the mixture was stirred at room temperature for 1.5 hours. The reaction mixture was concentrated in vacuo and the residue was chromatographed on a silica gel column (200 g), eluted with toluene (1.5 L) and toluene-ethyl acetate (10:1). The desired fractions were combined and concentrated to yield 10.3 g (71%) of the title compound IX-1.

Rf: 0.34 (chloroform/ethyl acetate=20/1; silica gel plate)

IR: $\nu_{max}^{KBr}$ cm$^{-1}$ 1780, 1710, 1660, 1510.

NMR: $\delta^{CDCl3+D2O}$ ppm 3.53 (2H, s, 2-H), 3.96 (2H, d, 7 Hz, —CH$_2$Cl), 4.05 (3H, s, —OCH$_3$), 5.03 (1H, d, 4.5 Hz, 6-H), 5.87 (1H, d, 4.5 Hz, 7-H), 6.70 (1H, s, thiazole-H), 6.96 (1H, s, —CHPh$_2$), 7.30 (25H, s, phenyl-H).

Preparation No. 19

Diphenylmethyl 3-(3-Iodo-1-propen-1-yl)-7-[(Z)-2-methoxyimino-2-(2-tritylaminothiazol-4-yl)acetamido]-3-cephem-4-carboxylate (X-1)

A mixture of the chloropropenyl derivative IX-1 (1.9 g, 2.3 mmoles) and sodium iodide (1.0 g, 6.9 mmoles) in acetone (40 ml) was stirred at room temperature for 1 hour. The reaction mixture was concentrated in vacuo and the residue was dissolved in ethyl acetate (50 ml). The ethyl acetate solution was washed with 10% aqueous sodium thiosulfate (50 ml) and aqueous sodium chloride (50 ml), dried over sodium sulfate and concentrated to give 2.0 g (94%) of the title compound X-1.

Rf: 0.34 (chloroform/ethyl acetate=20/1; silica gel plate).

IR: $\nu_{max}^{KBr}$ cm$^{-1}$ 1770, 1710, 1660, 1500.

NMR: $\delta^{CDCl3+D2O}$ ppm 3.50 (2H, s, 2-H), 3.84 (2H, d, 7 Hz, —HC=CH—CH$_2$I), 4.03 (3H, s, —OCH$_3$), 5.05 (1H, d, 4.5 Hz, 6-H), 5.90 (1H, d, 4.5 Hz, 7-H), 6.75 (1H, s, thiazole-H), 6.98 (1H, s, —CHPh$_2$), 7.30 (25H, s, phenyl-H).

Preparation No. 20

Diphenylmethyl 7-[(Z)-2-(2-t-Butoxycarbonyl-2-propoxyimino)-2-(2-tritylaminothiazol-4-yl)acetamido]-3-triphenylphosphoniomethyl-3-cephem-4-carboxylate Iodide (VIII-4')

A mixture of diphenylmethyl 7-[(Z)-2-(2-t-butoxycarbonyl-2-propoxyimino)-2-(2-tritylaminothiazol-4-yl)acetamido]-3-iodomethyl-3-cephem-4-carboxylate (VII-4', 5.3 g, 5 mmoles) and triphenylphosphine (2.6 g, 10 mmoles) in benzene (100 ml) was stirred at room temperature for 1 hour and diluted with diisopropyl ether. The resulting precipitate was collected by filtration to yield 6.0 g (91%) of the title compound VIII-4'.

IR: $\nu_{max}^{KBr}$ cm$^{-1}$ 1780, 1705, 1670, 1500.

Preparation No. 21

Diphenylmethyl 7-[(Z)-2-(2-t-Butoxycarbonyl-2-propoxyimino)-2-(2-tritylaminothiazol-4-yl)acetamido]-3-(3-chloro-1-propen-1-yl)-3-cephem-4-carboxylate (IX-4')

The phosphonium iodide (VIII-4', 5.7 g, 4.3 mmoles) in chloroform (100 ml) was treated with aqueous sodium hydroxide (0.34 g NaOH in 100 ml of water) at room temperature. The mixture was washed with water (150 ml) and dried over sodium sulfate. To the chloroform solution was added chloroacetaldehyde (0.5 g, 6.5 mmoles) and the mixture was stirred at room temperature for 1 hour. The reaction mixture was concentrated in vacuo and the residue was chromatographed on a silica gel column (120 g), eluted with benzene (500 ml) and benzene-ethyl acetate (10:1). The desired fractions were combined and concentrated to yield 2.6 g (61%) of IX-4'.

Rf: 0.18 (benzene/ethyl acetate=20/1; silica gel plate).

IR: $\nu_{max}^{KBr}$ cm$^{-1}$ 1785, 1720, 1690, 1520.

UV: $\lambda_{max}^{EtOH}$ nm($\epsilon$) 240 (sh, 23400), 278 (16000).

Preparation No. 22

Diphenylmethyl 7-[(Z)-2-(2-t-Butoxycarbonyl-2-propoxyimino)-2-(2-tritylaminothiazol-4-yl)acetamido]-3-(3-iodo-1-propen-1-yl)-3-cephem-4-carboxylate (X-4')

A mixture of the chloropropenyl derivative IX-4' (2.4 g, 2.4 mmoles) and sodium iodide (1.1 g, 7.2 mmoles) in acetone (50 ml) was stirred at room temperature for 1 hour. The reaction mixture was concentrated in vacuo and the residue was dissolved in ethyl acetate (50 ml). The ethyl acetate solution was washed with 10% aqueous sodium thiosulfate (50 ml), water (50 ml) and aqueous NaCl solution (50 ml), dried over sodium sulfate and concentrated to yield 2.4 g (93%) of X-4'.

IR: $\nu_{max}^{KBr}$ cm$^{-1}$ 1775, 1710, 1670, 1500.

Preparation No. 23

Diphenylmethyl 7-[(Z)-2-(1-t-Butoxycarbonylcyclobut-1-oxyimino)-2-(2-tritylaminothiazol-4-yl)acetamido]-3-triphenylphosphoniomethyl-3-cephem-4-carboxylate Iodide (VIII-5')

A mixture of diphenylmethyl 7-[(Z)-2-(1-t-butoxycarbonylcyclobut-1-oxyimino)-2-(2-tritylaminothiazol-4-yl)acetamido]-3-iodomethyl-3-cephem-4-carboxylate (VII-5', 6.4 g, 6 mmoles) and triphenylphosphine (2.4 g, 9 mmoles) in benzene (120 ml) was stirred at room temperature for 2 hours and diluted with n-hexane (ca. 500 ml). The resulting precipitate was collected by filtration to afford 7.5 g (94%) of the title compound VIII-B 5'.

IR: $\nu_{max}^{KBr}$ cm$^{-1}$ 1780, 1710, 1670, 1510.

Preparation No. 24

Diphenylmethyl 7-[(Z)-2-(1-t-Butoxycarbonylcyclobut-1-oxyimino)-2-(2-tritylaminothiazol-4-yl)acetamido]-3-(3-chloro-1-propen-1-yl)-3-cephem-4-carboxylate (IX-5')

The phosphonium iodide VIII-5' (7.4 g, 5.5 mmoles) in chloroform (150 ml) was treated with aqueous sodium hydroxide (0.44 g NaOH in 150 ml of water) at room temperature. The mixture was washed with water and dried over sodium sulfate. To the chloroform solution was added chloroacetaldehyde (863 mg, 11 mmoles) and the mixture was stirred at room temperature for 1.5 hours. The reaction mixture was concentrated in vacuo and the residue was chromatographed on a silica gel column (150 g), eluted with benzene (500 ml) and benzene-ethyl acetate (10:1). The desired fractions were combined and concentrated to give 2.95 g (53%) of the title compound IX-5'. M.p. 22 110° C. (dec.).

Rf: 0.61 (chloroform/ethyl acetate=20/1; silica gel plate).

IR: $\nu_{max}^{KBr}$ cm$^{-1}$ 1780, 1720, 1685, 1520.

UV: $\lambda_{max}^{EtOH}$ nm($\epsilon$) 240 (24700), 296 (15200).

Preparation No. 25

Diphenylmethyl 7-[(Z)-2-(1-t-Butoxycarbonylcyclobut-1-oxyimino)-2-(2-tritylaminothiazol-4-yl)acetamido]-3-(3-iodo-1-propen-1-yl)-3-cephem-4-carboxylate (X-5').

A mixture of the chloropropenyl derivative IX-5' (3.5 g, 3.5 mmoles) and sodium iodide (1.0 g, 7.0 mmoles) in acetone (70 ml) was stirred at room temperature for 1 hour. After evaporation of the solvent, the residue was dissolved in ethyl acetate (100 ml) and the solution was washed with 10% aqueous sodium thiosulfate (100 ml) and aqueous NaCl solution (100 ml), dried over sodium sulfate and concentrated under reduced pressure to afford 3.3 g (86%) of X-5'.

IR: $\nu_{max}^{KBr}$ cm$^{-1}$ 1780, 1720, 1680, 1520.

UV: $\lambda_{max}^{EtOH}$ nm($\epsilon$) 308 (17900).

EXAMPLE 1

7-[(Z)-2-(2-Aminothiazol-4-yl)-2-methoxyiminoacetamido]-3-[(E)-3-(1-methylpyrrolidinio)-1-propen-1-yl]-3-cephem-4-carboxylate (I-1A)

N-Methylpyrrolidine (0.2 ml, 2 mmole) was added to a suspension of diphenylmethyl 3-(3-iodo-1-propen-1-yl)-7-[(Z)-2-methoxyimino-2-(2-tritylaminothiazol-4-yl)acetamido]-3-cephem-4-carboxylate (X-1, 958 mg, 1 mmole) in ether (100 ml) and the mixture was stirred at room temperature for 1 hour. The reaction mixture was filtered, the filter cake was treated with 90% trifluoroacetic acid (5 ml) at room temperature for 1 hour, and the resulting mixture was concentrated under reduced pressure to give a light yellow powder (500 mg). The crude product was dissolved in formic acid (2 ml) and placed on a column of HP-20 resin (40 ml). The column was washed with water (about 500 ml) until the pH of the eluate became 7 and then was eluted with 30% aqueous CH$_3$OH. The eluate was monitored by UV absorption at 254 nm. The fractions containing the desired product were combined, concentrated and lyophilized to give 185 mg of light yellow powder. It was purified by HPLC (Lichrosorb RP-18; 20% methanol)

to give 101 mg (20%) of the title compound I-1A. M.p. >160° C. (dec.).

UV: $\lambda_{max}^{Phosphate\ buffer\ pH\ 7}$ nm($\epsilon$) 232 (15600), 292 (23400).

NMR: $\delta^{D_2O}$ ppm 2.27 (4H, m, pyrrolidine-H), 3.08 (3H, s, N-CH$_3$), 3.53 (4H, m, pyrrolidine-H), 3.76 (2H, s, 2-H), 4.06 (3H, s, OCH$_3$), 5.32 (1H, d, 4.5 Hz, 6-H), 5.82 (1H, d, 4.5 Hz, 7-H), 6.00 (1H, m, —CH=CH—CH$_2$—), 6.95 (1H, d, 16 Hz, —C$\underline{H}$=CH—CH$_2$—), 7.05 (1H, s, thiazole-H).

EXAMPLE 2

7-[(Z)-2-(2-Aminothiazol-4-yl)-2-methoxyiminoacetamido]-3-[(E)-3-pyridinio-1-propen-1-yl]-3-cephem-4-carboxylate (I-1B)

A mixture of diphenylmethyl 3-(3-iodo-1-propen-1-yl)-7-[(Z)-2-methoxyimino-2-(2-tritylaminothiazol-4-yl)acetamido]-3-cephem-4-carboxylate (X-1, 507 mg, 0.55 mmole) and pyridine (0.09 ml, 1.1 mmoles) in dichloromethane (10 ml) was allowed to stand at room temperature for 2.5 hours and was then diluted with diisopropyl ether (30 ml). The resulting precipitate was collected by filtration and treated with trifluoroacetic acid (5 ml) and anisole (1 ml) at room temperature for 1 hour, and the resulting mixture was concentrated under reduced pressure. The residue was triturated with ether and purified by column chromatography (HP-20; eluted with 10% and 30% methanol) and HPLC (Lichrosorb; 25% methanol). The desired fractions of the eluate were concentrated and lyophilized to afford 15 mg (4%) of I-1B.

UV: $\nu_{max}^{Phosphate\ buffer\ pH\ 7}$ nm($\epsilon$) 234 (16400), 259 (16600), 265 (16300), 292 (20400).

NMR: $\delta^{D_2O+NaHCO_3}$ ppm 3.72 (2H, s, 2-H), 4.08 (3H, s, OCH$_3$), 5.32 (1H, d, 4 Hz, 6-H), 5.38 (2H, d, 7 Hz, —CH=CH—CH$_2$—), 5.87 (1H, d, 4 Hz, 7-H), 6.15 (1H, td, 7 & 16 Hz, —CH=C$\underline{H}$-CH$_2$—), 6.95 (1H, d, 16 Hz, —C$\underline{H}$=CH—CH$_2$—), 7.06 (1H, s, thiazole-H), 8.13 (2$\overline{H}$, dd, 6 & 8 Hz, pyridine-3,5-H), 8.57 (1H, d, 8 Hz, pyridine-4-H), 8.90 (2H, d, 6 Hz, pyridine-2,6-H).

EXAMPLE 3

7-[(Z)-2-(2-Aminothiazol-4-yl)-2-(2-carboxy-2-propoxyimino)acetamido]-3-[(E)-3-pyridinio-1-propen-1-yl]-3-cephem-4-carboxylate (I-4B)

A mixture of diphenylmethyl 7-[(Z)-2-(2-t-butoxycarbonyl-2-propoxyimino)-2-(2-tritylaminothiazol-4-yl)acetamido]-3-(3-iodo-1-propen-1-yl)-3-cephem-4-carboxylate (X-4', 497 mg, 0.5 mmole) and pyridine (0.08 ml, 1 mmole) in dichloromethane (5 ml) was allowed to stand at room temperature for 3.5 hours, and was then diluted with diisopropyl ether. The resulting precipitate was collected by filtration and treated with trifluoroacetic acid (5 ml) and anisole (1 ml) at room temperature for 1 hour, and the resulting mixture was concentrated and triturated with ether to give crude product I-4B which was purified by HP-20 column chromatography, eluted with water (300 ml), 10% methanol (500 ml) and 30% methanol (300 ml). The eluate of 30% methanol was concentrated to a small volume, adjusted to pH 7 with sodium bicarbonate and lyophilized to afford 23 mg (7%) of the title compound I-4B. M.p. >150° C.

NMR: $\delta^{D_2O}$ ppm 1.60 (6H, s, —(CH$_3$)$_2$), 3.72 (2H, s, 2-H), 5.35 (3H, m, 6-H and CH=CH—CH$_2$—), 5.93 (1H, d, 4.5 Hz, 7-H), 6.15 (1H, m, —CH=C$\underline{H}$—CH$_2$—), 6.95 (1H, d, 16 Hz, —C$\underline{H}$=CH—CH$_2$—), 7.05 (1H, s, thiazole-H), 8.0–9.0 (5$\overline{H}$, m, pyridine-H).

EXAMPLE 4

7-[(Z)-2-(2-Aminothiazol-4-yl)-4-yl)-2-(1-carboxycyclobut-1-oxyimino)acetamido]-3-[(E)-3-(1-methylpyrrolidinio)-1-propen-1-yl]-3-cephem 4-carboxylate (I-5A)

1-Methylpyrrolidine (61 mg, 0.72 mmole) was added to a suspension of diphenylmethyl 7-[(Z)-2-(1-t-butoxycarbonylcyclobut-1-oxyimino)-2-(2-tritylaminothiazol-4-yl)acetamido]-3-(3-iodo-1-propen-1-yl)-3-cephem-4-carboxylate (X-5', 714 mg, 0.65 mmole) in ether and the mixture was stirred at room temperature for 1 hour. The reaction mixture was filtered and the filter cake (ca. 500 mg) was treated with 90% trifluoroacetic acid (5 ml) and anisole (1 ml) at room temperature for 1 hour. The resulting mixture was concentrated and the residue was triturated with ether to give 308 mg of the crude product I-5A. It was purified by HP-20 column chromatography eluted with water (200 ml), 10% methanol and 30% methanol. The eluate of 30% methanol was concentrated to a small volume and lyophilized to give 123 mg (57%) of I-5A. M.p. >160° C. (dec.).

IR: $\nu_{max}^{KBr}$ cm$^{-1}$ 1760, 1660, 1600, 1530, 1390.

UV: $\lambda_{max}^{Phosphate\ buffer\ pH\ 7}$ nm($\epsilon$) 235 (14000), 292 (24000).

NMR: $\delta^{D_2O}$ ppm 1.8–2.7 (10H, m, cyclobutyl-H & pyrrolidine-H), 3.57 (4H, m, pyrrolidine-H), 3.80 (2H, s, 2-H), 4.10 (2H, d, 7 Hz, —CH=CH—CH$_2$—), 5.38 (1H, d, 4 Hz, 6-H), 5.93 (1H, d, 4 Hz, 7-H), 6.02 (1H, dt, 16 & 7 Hz, —CH=C$\underline{H}$—CH$_2$—), 7.00 (1H, d, 16 Hz, —C$\underline{H}$=CH—CH$_2$—), 7.12 (1H, s, thiazole-H).

EXAMPLE 5

7-[(Z)-2-(2-Aminothiazol-4-yl)-2-(1-carboxycyclobut-1-oxyimino)acetamido]-3-[(E)-3-pyridinio-1-propen-1-yl]-3-cephem-4-carboxylate (I-5B)

Pyridine (0.1 ml, 1.2 mmole) was added to a solution of diphenylmethyl 7-[(Z)-2-(1-t-butoxycarbonylcyclobut-1-oxyimino)-2-(2-tritylaminothiazol-4-yl)acetamido]-3-(3-iodo-1-propen-1-yl)-3-cephem-4-carboxylate (X-5', 659 mg, 9.6 mmole) in dichloromethane (7 ml). The mixture was stirred at room temperature for 2.5 hours and diluted with diisopropyl ether. The resulting solid (383 mg) was collected by filtration and treated with 90% trifluoroacetic acid (5 ml) and anisole (1 ml) at room temperature for 1 hour. The resulting mixture was concentrated and the residue was triturated with ether to give 237 mg of crude I-5B, which was purified by HP-20 column chromatography [eluted with water (150 ml), 10% methanol (200 ml) and 30% methanol (500 ml)]. The eluate of 30% methanol was concentrated to a small volume, adjusted to pH 7 with sodium bicarbonate and lyophilized to afford 72 mg (21%) of I-5B. M.P. >160° C. (dec.).

IR: $\nu_{max}^{KBr}$ cm$^{-1}$ 1760, 1660, 1590, 1530, 1390.

UV: $\lambda_{max}^{Phosphate\ buffer\ pH\ 7}$ nm($\epsilon$) 259 (16600), 266 (16800), 292 (22000).

NMR: $\delta^{D_2O}$ ppm 1.8–2.9 (6H, m, cyclobutyl-H), 3.75 (2H, s, 2-H), 5.37 (1H, d, 4 Hz, 6-H), 5.40 (2H, d, 7 Hz, —CH=CH—CH$_2$—), 5.93 (1H, d, 4 Hz, 7-H), 6.18 (1H, dt, 16 & 17 Hz, —CH=C$\underline{H}$—CH$_2$—), 6.98 (1H, d, 16 Hz, —C$\underline{H}$=CH—CH$_2$—), 7.15 (1H, s, thiazole-H), 8.0–9.0 (5$\overline{H}$, m, pyridine-H).

EXAMPLE 6

7-[(Z)-2-(2-Aminothiazol-4-yl)-2-(1-carboxycyclobut-1-oxyimino)acetamido]-3-[(E)-3-(2-amino-5-thiazolo[4,5-c]pyridinio)-1-propen-1-yl]-3-cephem-4-carboxylate (I-5C)

A mixture of diphenylmethyl 7-[(Z)-2-(1-t-butoxycarbonylcyclobut-1-oxyimino)-2-(2-tritylaminothiazol-4-yl)acetamido]-3-(3-iodo-1-propen-1-yl)-3-cephem-4-carboxylate (X-5', 641 mg, 0.58 mmole) and 2-aminothiazolo[4,5-c]pyridine (97 mg, 0.64 mmole) in dimethylsulfoxide (10 ml) was stirred at room temperature for 1 hour. The reaction mixture was diluted with ethyl acetate (150 ml), washed with water (2×150 ml), dried over sodium sulfate and concentrated under reduced pressure. The oily residue was triturated with diisopropyl ether and the resulting precipitate (558 mg) was treated with a mixture of 90% trifluoroacetic acid (10 ml) and anisole (2 ml) at room temperature for 1 hour. Concentration of the mixture followed by trituration of the residue with ether gave 313 mg of crude I-5C, which was purified by column chromatography [HP-20, eluted with 30% and 50% $CH_3OH$: the packing in the PrepPAK-500/$C_{18}$ (Waters), eluted with 10% $CH_3OH$] to give 40 mg (11%) of I-5C. M.p. >150° C. (dec.).

NMR: $\delta^{D_2O}$ ppm 1.5–2.8 (6H, m, cyclobutane-H), 3.73 (2H, s, 2-H), 5.47 (1H, d, 4.5 Hz, 6-H), 5.90 (1H, d, 4.5 Hz, 7-H), 6.20 (1H, m, —CH=CH—CH$_2$—), 6.98 (1H, d, 15 Hz, —CH=CH—CH$_2$—), 7.02 (1H, s, thiazole-H), 8.25 (1H, d, 6 Hz, pyridine-H), 8.40 (1H, d, 6 Hz, pyridine-H), 8.74 (1H, s, pyridine-H).

EXAMPLE 7

7-[(Z)-2-(2-Aminothiazol-4-yl)-2-methoxyiminoacetamido]-3-[(E)-3-trimethylammonio-1-propen-1-yl]-3-cephem-4-carboxylate (I-1D)

Trimethylamine hydrochloride (6.31 g, 66 mmole) was added to an aqueous NaOH solution (2N, 33 ml) covered with ethyl acetate (100 ml). The organic layer was separated, dried over NaOH pellets, and added to a suspension of diphenylmethyl 3-(3-iodo-1-propen-1-yl)-7-[(Z)-2-methoxyimino-2-(2-tritylaminothiazol-4-yl)acetamido]-3-cephem-4-carboxylate (X-1, 32 g, 33 mmole) in a mixture of ethyl acetate and n-hexane (300 ml/150 ml). The mixture was stirred for one hour at room temperature and then filtered to give the blocked title compound, which was treated with trifluoroacetic acid (50 ml) and anisole (10 ml) for one hour at room temperature. The mixture was concentrated under reduced pressure and the residue was triturated with ether to give 10.3 g of dark brown solid, which was treated with water (100 ml) at room temperature. After removal of insolubles by filtration, the filtrate was chromatographed on a column of HP-20 (200 ml) by eluting with 30% aqueous methanol. The eluate was concentrated and lyophilized to give 2.3 g of the crude title compound, which was purified by preparative HPLC (Waters Associates, System 500, PrepPAK 500/$C_{18}$, 15% $CH_3OH$) to afford 880 mg (5%) of the title compound I-1D. Estimated purity 75% (by HPLC).

Further Purification

The above product (850 mg of free base; estimated purity 75%) was dissolved in 1N $H_2SO_4$ (2 ml), treated with active carbon (20 mg), filtered and washed with 1N $H_2SO_4$ (1.5 ml). To the combined filtrate and washings was added acetone (5 ml), to give an oily product. The oily solid was removed by decantation and triturated with acetone to give 420 mg of light yellow powder (75% pure). The supernatant was poured into acetone (150 ml) and the mixture was stirred for 10 minutes at room temperature. The resulting precipitate was collected by filtration to afford 612 mg of white powder. Estimated purity 90%.

IR: $\nu_{max}^{KBr}$ cm$^{-1}$ 1780, 1670, 1635, 1390, 1120.

UV: $\lambda_{max}^{Phosphate\ buffer\ (pH\ 7)}$ nm($\epsilon$) 235 (16000), 293 (25000).

|  | H | N | S |
|---|---|---|---|
| Calc'd. for $C_{19}H_{24}N_6O_5S_2.H_2SO_4.H_2O$: | 38.25 | 4.73 | 14.09 | 16.12 |
| Found | 38.81 | 4.78 | 13.62 | 15.63 |

EXAMPLE 8

7-[(Z)-2-(2-Aminothiazol-4-yl)-2-methoxyiminoacetamido]-3-[(E)-3-(3-aminopyridinio)-1-propen-1-yl]-3-cephem-4-carboxylate (I-1E)

A mixture of diphenylmethyl 7-[(Z)-2-(2-tritylaminothiazol-4-yl)-2-methoxyiminoacetamido]-3-(3-iodo-1-propen-1-yl)-3-cephem-4-carboxylate (X-1, 738 mg, 0.8 mmole) and 3-aminopyridine (113 mg, 1.2 mmole) in methylene chloride (15 ml) was stirred at room temperature for 1.5 hours and then concentrated under reduced pressure. The residue was triturated with diisopropyl ether and treated with a mixture of 90% trifluoroacetic acid (TFA) (8 ml) and anisole (1.6 ml) at room temperature for 1 hour, and then was concentrated and triturated with ether. The resulting crude product was purified by column chromatography using HP-20 (eluted with 10% methanol and 30% methanol) and the packing in a PrepPAK-500/$C_{18}$ cartridge (Waters) (eluted with 5% methanol). The desired fraction was concentrated and lyophilized to give 38 mg (9%) of the title compound (I-1E). Estimated purity, 55%. M.p. >170° C. (dec.).

IR: $\nu_{max}^{KBr}$ cm$^{-1}$ 1760, 1660 (sh), 1600, 1540.

UV: $\lambda_{max}^{Phosphate\ buffer\ pH\ 7}$ nm($\epsilon$) 217 (28300), 253 (18600), 292 (23400).

EXAMPLE 9

7-[(Z)-2-(2-Aminothiazol-4-yl)-2-methoxyiminoacetamido]-3-[(E)-3-(4-amino-1-pyridinio)-1-propen-1-yl]-3-cephem-4-carboxylate (I-1I)

A mixture of X-1 (480 mg, 0.5 mmole) and 4-aminopyridine (94 mg, 1 mmole) in ether (50 ml) was stirred for one hour at room temperature. The reaction mixture was filtered to give 440 mg of the quaternary product, which was treated with aqueous 90% TFA for one hour at room temperature and then concentrated under reduced pressure at 15° C. The oily residue was triturated with isopropyl ether to give 350 mg of the TFA salt, which was dissolved in 85% formic acid and chromatographed on a column of Diaion HP-20 (40 ml) by eluting with 30% $CH_3OH$. The eluate was concentrated and lyophilized to give 52 mg of the crude product, which was purified by column chromatography using the packing in a PrepPAK-500/$C_{18}$ cartridge (Waters) (eluted successively with 5% $CH_3OH$, and 10% $CH_3OH$) to give 18 mg (7%) of the title compound (I-1I). Estimated purity, 70%.

IR: $\nu_{max}^{KBr}$ cm$^{-1}$ 1760, 1650, 1600, 1540.

UV: $\lambda_{max}^{Phosphate\ buffer\ pH\ 7}$ nm($\epsilon$) 230 (15500), 277 (26700), 285 (27000).

NMR: $\delta^{D2O}$ ppm 3.70 (2H, br-s), 4.08 (3H, s), 5.30 (1H, d, 4.0 Hz), 5.97 (1H, d, 4.0 Hz), 6.75 (1H, d, 16 Hz), 6.90 (2H, d, 7.0 Hz), 7.05 (1H, s), 8.02 (1H, d, 7.0 Hz).

EXAMPLE 10

7-[(Z)-2-(2-Aminothiazol-4-yl)-2-methoxyiminoacetamido]-3-[(E)-3-(4-carbamoyl-1-pyridinio)-1-propen-1-yl]-3-cephem-4-carboxylate (I-1J)

A mixture of X-1 (480 mg, 0.5 mmole) and isonicotinamide (244 mg, 1.0 mmole) in DMSO (20 ml) was stirred for one hour at room temperature. The reaction mixture was poured into water (100 ml) and extracted with ethyl acetate (3×50 ml). The combined extracts were washed with water, dried and concentrated to give 375 mg of the quaternary product, which was treated with 90% TFA for 3 hours at room temperature. The mixture was concentrated under reduced pressure at 15° C. and the oily residue was triturated with ether to give 240 mg of the TFA salt of the title compound, which was dissolved in 85% formic acid and chromatographed on a column of Diaion HP-20 (30 ml) by eluting with 30% CH₃OH. The eluate was concentrated and lyophilized to afford 25 mg (9%) of the title compound (I-1J). Estimated purity, 55%.

IR: $\nu_{max}^{KBr}$ cm⁻¹ 1760, 1660, 1605, 1530.

UV: $\lambda_{max}^{Phosphate\ buffer\ pH\ 7}$ nm($\epsilon$) 225 (19900), 292 (19400).

NMR: $\delta^{D2O}$ ppm 3.75 (2H, s), 4.07 (3H, s), 5.32 (1H, d, 4.0 Hz), 5.85 (1H, d, 4.0 Hz), 7.05 (1H, d, 16 Hz), 7.10 (1H, s), 8.43 (2H, d, 7.0 Hz), 9.10 (2H, d, 7.0 Hz).

EXAMPLE 11

7-[(Z)-2-(2-Aminothiazol-4-yl)-2-methoxyiminoacetamido]-3-[(E)-3-(2-methyl-3-thiazolio)-1-propen-1-yl]-3-cephem-4-carboxylate (I-1H)

To a mixture of X-1 (480 mg, 0.5 mmole) and 2-methylthiazole (0.1 ml) in methylene chloride (10 ml) was added silver tetrafluoroborate (90% pure, 50 mg) at −40° C. The mixture was stirred at −10° C. for 20 minutes and filtered through a layer of Dicalite (celite). The filtrate was evaporated under reduced pressure and the oily residue was triturated with isopropyl ether (50 ml) to give an amorphous powder (560 mg). The powder was treated with 90% TFA at room temperature for 1 hour. The mixture was concentrated under reduced pressure and the residue was triturated with ether (50 ml) to afford the TFA salt (350 mg) of the title compound. The salt was dissolved in 85% formic acid (5 ml) and chromatographed on an HP-20 column (30 ml) by eluting with 30% methanol. The eluate was concentrated and lyophilized to give 43 mg of amorphous powder, which was purified by HPLC (Column: Lichrosorb RP-18, 8×300 mm) eluting with 20% methanol to afford 13 mg (5%) of the title compound (I-1H). Estimated purity, 70%.

IR: $\nu_{max}^{KBr}$ cm⁻¹ 1765, 1600, 1535.

UV: $\lambda_{max}^{Phosphate\ buffer\ pH\ 7}$ nm($\epsilon$) 237 (19000), 292.5 (23700).

NMR: $\delta^{D2O}$ ppm 3.03 (3H, s), 3.72 (2H, s), 4.07 (3H, s), 5.22 (1H, d, 6.0 Hz), 5.87 (1H, d, 6.0 Hz), 6.71 (1H, d, 16 Hz), 7.07 (1H, s), 7.45 (1H, d, 4.0 Hz), 7.67 (1H, d, 4.0 Hz).

EXAMPLE 12

7-[(Z)-2-(2-Aminothiazol-4yl)-2-methoxyiminoacetamido]-3-[(E)-3-(2-methylthio-3-thiazolio)-1-propen-1-yl]-3-cephem-4-carboxylate (I-1G)

To a mixture of X-1 (480 mg, 0.5 mmole) and 2-methylthiothiazole (0.1 ml) in methylene chloride (10 ml) was added silver tetrafluoroborate (90% pure, 60 mg) at −40° C. The mixture was stirred at −10° C. for 10 minutes and filtered through a layer of Dicalite (celite). The filtrate was concentrated under reduced pressure and the oily residue was triturated with ether (50 ml) to give an amorphous solid (455 mg), which was dissolved in 90% TFA (3 ml) at −5° C. The mixture was stirred for one hour at room temperature and concentrated under reduced pressure at 10° C. The residue was triturated with ether to give 288 mg of the TFA salt of the desired product. A solution of the TFA salt in 85% formic acid (5 ml) was chromatographed on a column of Diaion HP-20 (30 ml) which was eluted with 30% methanol. The eluate was concentrated and lyophilized to give 50 mg of the amorphous crude product which was purified by column chromatography [the packing in a PrepPAK-500/C₁₈ cartridge (Waters), 50% methanol] and HPLC (Lichrosorb RP-18, 8×300 mm, 25% methanol) to give 9.8 mg (4%) of the title compound (I-1G). Estimated purity, 40%.

IR: $\nu_{max}^{KBr}$ cm⁻¹ 1760, 1660, 1600, 1540.

UV: $\lambda_{max}^{Phosphate\ buffer\ pH\ 7}$ nm($\epsilon$) 235 (16600), 290 (24800).

NMR: $\delta^{D2O}$ ppm 3.05 (3H, s), 3.71 (2H, s), 4.08 (3H, s), 5.32 (1H, d, 4.0 Hz), 5.97 (1H, d, 4.0 Hz), 6.80 (1H, d, 16 Hz), 7.07 (1H, s), 7.94 (1H, d, 4.0 Hz), 8.12 (1H, d, 4.0 Hz).

EXAMPLE 13

7-[(Z)-2-(2-Aminothiazol-4-yl)-2-methoxyiminoacetamido]-3-[(E)-3-(1-methyl-3-pyrrolinio)-1-propen-1-yl]-3-cephem-4-carboxylate (I-1F)

To a solution of X-1 (540 mg, 0.57 mmole) in a mixture of ethyl acetate (10 ml) and ether (10 ml) was added a 0.5M solution of N-methyl-3-pyrroline in ether (2.3 ml) [prepared from cis-1,4-dichloro-2-butene and methylamine according to the procedure of J. M. Bobbitt et al., J. Org. Chem., 25, 2230 (1960)]. After stirring at room temperature for 30 minutes, the mixture was diluted with ether (50 ml). The resulting precipitate was collected by filtration, washed with ether and dried to give the quanternary ammonium salt (280 mg), which was treated with 90% trifluoroacetic acid (3 ml) at room temperature for 1 hour. After evaporation of the solvent, the residue was triturated with ether to give the TFA salt. A solution of the TFA salt in a small amount of methanol was charged on an HP-20 column (50 ml) and the column was washed with water (500 ml) and eluted with 30% methanol (500 ml). The methanolic eluant was evaporated and lyophilized to give a crude product (60 mg), which was purified by HPLC (Lichrosorb RP-18, 8×300 mm, eluted with 20% methanol) to afford 16 mg (16%) of the title compound (I-1F). Estimated purity, 50%.

IR: $\nu_{max}^{KBr}$ cm⁻¹ 3400, 1760, 1600.

UV: $\lambda_{max}^{Phosphate\ buffer\ pH\ 7}$ nm($\epsilon$) 232 (15400), 293 (22500).

NMR: $\delta^{D2O}$ ppm 3.08 (3H, s, $\overset{+}{N}$—CH₃), 3.25 (4H, m,

-continued

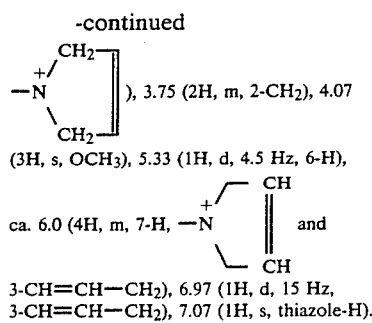
), 3.75 (2H, m, 2-CH$_2$), 4.07
(3H, s, OCH$_3$), 5.33 (1H, d, 4.5 Hz, 6-H), ca. 6.0 (4H, m, 7-H, —N⁺⟨CH=CH⟩) and 3-CH=CH—CH$_2$), 6.97 (1H, d, 15 Hz,
3-CH=CH—CH$_2$), 7.07 (1H, s, thiazole-H).

EXAMPLE 14

7-[(Z)-2-(2-Aminothiazol-4-yl)-2-(2-carboxy-2-propoxyimino)acetamido]-3-[(E)-3-(1-methylpyrrolidinio)-1-propen-1-yl]-3-cephem-4-carboxylate (I-4A)

A mixture of diphenylmethyl 7-[(Z)-2-(2-t-butoxycarbonyl-2-propoxyimino)-2-(2-tritylaminothiazol-4-yl)acetamido]-3-(3-iodo-1-propen-1-yl)-3-cephem-4-carboxylate (X-4') (543 mg, 0.5 mmole) and 1-methylpyrrolidine (47 mg, 0.55 mmole) in ether (30 ml) was stirred at room temperature for 1 hour. The resulting precipitate was collected by filtration and treated with 90% TFA (5 ml) and anisole (1 ml) at room temperature for 1 hour. After concentration of the reaction mixture, the residue was triturated with ether to give the crude TFA salt, which was purified by column chromatography [HP-20 (30 ml), eluted with water (300 ml) and 30% methanol (600 ml)]. The methanolic eluate was concentrated to a small volume, neutralized with sodium bicarbonate and lyophilized to yield 104 mg (35%) of the title compound (I-4A). Estimated purity, 65%.

IR: $\nu_{max}^{KBr}$ cm$^{-1}$ 1765, 1660, 1590, 1540.

UV: $\lambda_{max}^{Phosphate\ buffer\ pH\ 7}$ nm($\epsilon$) 228 (sh, 14900), 292 (23900).

NMR: $\delta^{D2O}$ ppm 1.55 (6H, s, —OC(CH$_3$)$_2$—), 2.22 (4H, m, pyrrolidine-H), 3.03 (3H, s, N—CH$_3$), 3.50 (4H, m, pyrrolidine-H), 3.70 (2H, s, 2-H), 4.00 (2H, d, 7 Hz, =CH—CH$_2$—), 5.28 (1H, d, 4.5 Hz, 6-H), 5.83 (1H, d, 4.5 Hz), 6.95 (1H, d, 15 Hz, —CH=CH—CH$_2$—), 7.00 (1H, s, thiazole-H).

EXAMPLE 15

7-[(Z)-2-(2-Aminothiazol-4-yl)-2-(2-carboxy-2-propoxyimino)acetamido]-3-[(E)-3-(2-methylthio-3-thiazolio)-1-propen-1-yl]-3-cephem-4-carboxylate (I-4G)

Silver tetrafluoroborate (156 mg, 0.8 mmole) was added to a solution of the iodopropenyl derivative X-4' (760 mg, 0.7 mmole) and 2-methylthiothiazole (120 mg, 0.9 mmole) under cooling in a dry ice-acetone bath. The mixture was stirred at −10° C. for 10 minutes and filtered, and the filtrate was concentrated and triturated with ether to give 782 mg of the quaternary salt. The product was treated with a mixture of 90% trifluoroacetic acid (8 ml) and anisole (2 ml) at room temperature for one hour, and the reaction mixture was concentrated and triturated with ether to give the crude product. It was purified by column chromatography with HP-20 (eluted with 30% methanol and 50% methanol) and subsequently with the packing in a PrepPAK-500/C$_{18}$ cartridge (Waters) (eluted with water) to afford 65 mg of the title compound (I-4G). Estimated purity, 60%. M.p. >100° C. (dec.).

IR: $\nu_{max}^{KBr}$ cm$^{-1}$ 1760, 1660 (sh), 1600, 1540.

UV: $\lambda_{max}^{Phosphate\ buffer\ pH\ 7}$ nm($\epsilon$) 233 (15700), 289 (28400).

NMR: $\delta^{D2O}$ ppm 1.65 (6H, s, —C(CH$_3$)$_2$—), 3.10 (3H, s, —SCH$_3$), 3.77 (2H, s, 2-H), 5.17 (2H, d, 7 Hz, =CH—CH$_2$—), 5.38 (1H, d, 4.5 Hz, 6-H), 5.93 (1H, d, 4.6 Hz, 7-H), 6.87 (1H, d, 15 Hz, —CH=CH—CH$_2$—), 7.10 (1H, s, thiazole-H), 8.00 & 8.17 (1H each, d, 4 Hz, thiazolio-H).

EXAMPLE 16

7-[(Z)-2-(2-Aminothiazol-4-yl)-2-(1-carboxycyclobut-1-oxyimino)acetamido]-3-[(E)-3-(4-aminopyridino)-1-propen-1-yl]-3-cephem-4-carboxylate (I-5I)

A suspension of diphenylmethyl 7-[(Z)-2-(1-t-butoxycarbonylcyclobut-1-oxyimino)-2-(2-tritylaminothiazol-4-yl)acetmido]-3-(3-iodo-1-propen-1-yl)-3-cephem-4-carboxylate (X-5') (714 mg, 0.65 mmole) and 4-aminopyridine (73 mg, 0.78 mmole) in ether (10 ml) was stirred at room temperature for 2 hours. The reaction mixture was filtered and the filter cake was treated with a mixture of 90% TFA (7 ml) and anisole (1 ml) at room temperature for 1 hour. The mixture was concentrated and triturated with ether, and the crude TFA salt was purified by chromatography on an HP-20 column, which was eluted with 30% methanol and 50% methanol. The fractions containing the desired product were combined, concentrated to a small volume, adjusted to pH 7 with sodium bicarbonate and lyophilized. The crude product was purified by column chromatography [the packing in a PrepPAK-500/C$_{18}$ cartridge (Waters), eluted with water] to afford 36 mg (9%) of the title compound (I-5I). Estimated purity, 80%. M.p. >140° C. (dec.).

IR: $\nu_{max}^{KBr}$ cm$^{-1}$ 1760, 1650, 1590, 1540.

UV: $\lambda_{max}^{Phosphate\ buffer\ pH\ 7}$ nm($\epsilon$) 287 (29700).

NMR: $\delta^{D2O}$ ppm 1.5–3.0 (6H, m, cyclobutyl-H), 3.76 (2H, s, 2-H), 5.38 (1H, 4 Hz, 6-H), 5.95 (1H, d, 4 Hz, 7-H), 7.12 (1H, s, thiazole-H), 6.95 & 8.07 (2H each, d, 7 Hz, pyridine-H).

EXAMPLE 17

7-[(Z)-2-(2-Aminothiazol-4-yl)-2-(1-carboxycyclobut-1-oxyimino)acetamido]-3-[(E)-3-(3-amino-1-pyridinio)-1-propen-1-yl]-3-cephem-4-carboxylate (I-5E)

A mixture of the 3-iodopropenyl derivative X-5' (500 mg, 0.45 mmole) and 3-aminopyridine (51 mg, 0.54 mmole) in ether (10 ml) was stirred at room temperature for 16 hours. The resulting precipitate was collected by filtration and treated with a mixture of 90% trifluoroacetic acid (5 ml) and anisole (1 ml) at room temperature for 1 hour. The mixture was concentrated in vacuo and triturated with ether. The solid was collected by filtration and purified by column chromatography using HP-20 (eluted with 30% methanol and 50% methanol) and the packing in a PrepPAK-500/C$_{18}$ cartridge (Waters) (eluted with water). The desired fraction was concentrated to a small volume and lyophilized to yield 85 mg (28%) of the title compound (I-5E). Estimated purity, 80%. M.p. >140° C. (dec.).

IR: $\nu_{max}^{KBr}$ cm$^{-1}$ 1760, 1660 (sh), 1580.

UV: $\lambda_{max}^{Phosphate\ buffer\ pH\ 7}$ nm($\epsilon$) 216 (31800), 253 (20700), 294 (27600).

NMR: $\delta^{D2O}$ ppm 1.7–2.9 (6H, m, cyclobutyl-H), 3.73 (2H, s, 2-H), 5.18 (2H, d, 8 Hz, =CH—CH$_2$—), 5.36 (1H, d, 4 Hz, 6-H), 5.92 (1H, d, 4 Hz, 7-H), 6.12 (1H, dt, 8 & 16 Hz, —CH=CH—CH$_2$—), 6.96 (1H, d, 16 Hz, —CH=CH—CH$_2$—), 7.06 (1H, s, thiazole-H), 7.5–8.2 (4H, m, pyridine-H).

EXAMPLE 18

7-[(Z)-2-(2-Aminothiazol-4-yl)-2-(1-carboxycyclobut-1-oxyimino)acetamido]-3-[(E)-3-(2-methylthio-3-thiazolio)-1-propen-1-yl]-3-cephem-4-carboxylate (I-5G)

A solution of the 3-iodopropenyl derivative X-5' (878 mg, 0.8 mmole) and 2-methylthiothiazole (0.2 ml, 2 mmole) in methylene chloride (16 ml) was cooled in a dry ice-acetone bath. To the solution was added silver tetrafluoroborate (235 mg, 1.2 mmole). The mixture was stirred at −10° C. for 10 minutes and filtered. The filtrate was concentrated and the residue was triturated with ether to give the quaternary derivative. The product was treated with a mixture of TFA (8 ml) and anisole (2 ml) at room temperature for 1 hour. The reaction mixture was concentrated and triturated with ether to give 460 mg of the crude product, which was purified by column chromatography using HP-20 (30% methanol and 50% methanol) and the packing of a PrepPAK-500/C$_{18}$ cartridge (Waters) to yield 50 mg (10%) of the title compound (I-5G). Estimated purity, 60%. M.p. >110° C. (dec.).

IR: $\nu_{max}^{KBr}$ cm$^{-1}$ 1760, 1660 (sh), 1590, 1540.

UV: $\lambda_{max}^{Phosphate\ buffer\ pH\ 7}$ nm($\epsilon$) 237 (15700), 290 (31500).

NMR: $\delta^{D_2O}$ ppm 1.5–2.3 (6H, m, cyclobutyl-H), 3.05 (3H, s, —SCH$_3$), 3.70 (2H, s, 2-H), 5.07 (2H, d, 6 Hz, =CH—CH$_2$—N), 5.33 (1H, d, 4.5 Hz, 6-H), 5.88 (1H, d, 4.5 Hz, 7-H̄), 6.00 (1H, m, —CH=CH—CH$_2$), 6.80 (1H, d, 16 Hz, —CH=CH—CH$_2$), 7.07 (1H, s, thiazole-H), 7.93 & 8.13 (1H̄, each d, 4 Hz, thiazolio-H).

EXAMPLE 19

7-[(Z)-2-(2-Aminothiazol-4-yl)-2-(1-carboxycyclobut-1-oxyimino)acetamido]-3-[(E)-3-(1-methyl-3-pyrrolinio)-1-propen-1-yl]-3-cephem-4-carboxylate (I-5F)

To a solution of X-5' (770 mg, 0.70 mmole) in a mixture of ethyl acetate (5 ml) and ether (25 ml) was added a 0.2M solution of N-methyl-3-pyrroline in ether (7 ml) and the mixture was stirred at room temperature for 30 minutes. To the reaction mixture was added ether (5 ml) to afford precipitate, which was collected by filtration, washed with ether, and dried to give the quaternary salt (430 mg). It was deblocked with 90% TFA (5 ml) at room temperature for 1 hour. Concentration of the mixture followed by the addition of ether gave the TFA salt, which was subjected to HP-20 column chromatography (50 ml), eluted with water (500 ml) and 30% methanol (500 ml). The methanolic eluant was evaporated and lyophilized to give the crude product (115 mg), which was purified by HPLC (Lichrosorb RP-18, 8×300 mm, eluant 5% methanol) to afford 78 mg (19%) of the title compound (I-5F). Estimated purity, 85%. M.p. >140° C. (dec.).

IR: $\nu_{max}^{KBr}$ cm$^{-1}$ 3400, 1760, 1580.

UV: $\lambda_{max}^{Phosphate\ buffer\ pH\ 7}$ nm($\epsilon$) 238 (13600), 293 (23500).

NMR: $\delta^{D_2O}$ ppm ca. 2.1 & 2.5 (6H, m, cyclobutyl-H), 3.10 (3H, s, —N—CH$_3$), 3.27 (4H, m, 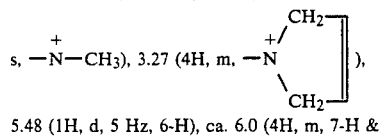 ), 5.48 (1H, d, 5 Hz, 6-H), ca. 6.0 (4H, m, 7-H &

3-CH=CHCH$_2$—N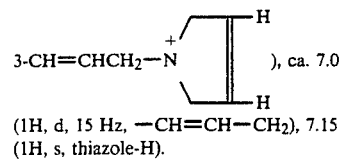 ), ca. 7.0

(1H, d, 15 Hz, —CH=CH—CH$_2$), 7.15 (1H, s, thiazole-H).

EXAMPLE 20

7-[(Z)-2-(2-Aminothiazol-4-yl)-2-methoxyiminoacetamido]-3-[(E)-3-(2-amino-5-thiazolo[4,5-c]pyridinio)-1-propen-1-yl]-3-cephem-4-carboxylate (I-1C)

To a solution of X-1 (876 mg, 0.91 mmole) in DMSO (2 ml) was added 2-aminothiazolo[4,5-c]pyridine (116 mg, 0.77 mmole) and the mixture was stirred at room temperature for 1 hour. The solution was diluted with ethyl acetate (200 ml) and the resulting precipitate was collected by filtration to give 240 mg of the quaternary salt. The product was treated with 90% aqueous TFA (3 ml) and the mixture was stirred at room temperature for 1 hour. The mixture was concentrated in vacuo, triturated with isopropyl ether and filtered to afford 167 mg of brown powder, which was dissolved in water (25 ml) at room temperature. After removal of insolubles by filtration, the filtrate was chromatographed on a column of the packing in a PrepPAK-500/C$_{18}$ cartridge (Waters), which was eluted with water, 10% aqueous methanol and 20% methanol, successively. The fractions containing the desired product (monitored by UV, 254 nm) were combined, concentrated and lyophilized to give 20 mg (16%) of the title compound (I-1C). Estimated purity, 95% by HPLC.

IR: $\nu_{max}^{KBr}$ cm$^{-1}$ 1760, 1630, 1600, 1535, 1480.

UV: $\lambda_{max}^{Phosphate\ buffer\ (pH\ 7)}$ nm($\epsilon$) 246 (49600), 292 (27900).

EXAMPLE 21

7-[(Z)-2-(2-Aminothiazol-4-yl)-2-(1-carboxycyclobut-1-oxyimino)acetamido]-3-[(E)-3-(2-methyl-3-thiazolio)-1-propen-1-yl]-3-cephem-4-carboxylate (I-5H)

The general procedure of Example 11 is repeated except that the diphenylmethyl 7-[(Z)-2-(2-tritylaminothiazol-4-yl)-2-methoxyiminoacetamido]-3-(3-iodo-1-propen-1-yl)-3-cephem-4-carboxylate (X-1) utilized therein is replaced by an equimolar amount of diphenylmethyl 7-[(Z)-2-(1-t-butoxycarbonylcyclobut-1-oxyimino)-2-(2-tritylaminothiazol-4-yl)acetamido]-3-(3-iodo-1-propen-1-yl)-3-cephem-4-carboxylate (X-5'), and the title product is thereby produced.

We claim:

1. A compound of the formula

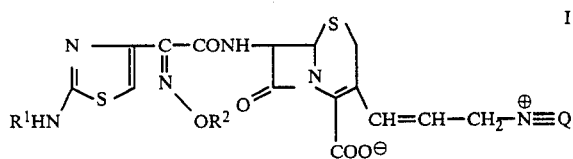

wherein R$^1$ is hydrogen or a conventional amino-protecting group, R$^2$ is hydrogen, a straight or branched chain alkyl group containing from 1 to 4 carbon atoms, or a group of the formula

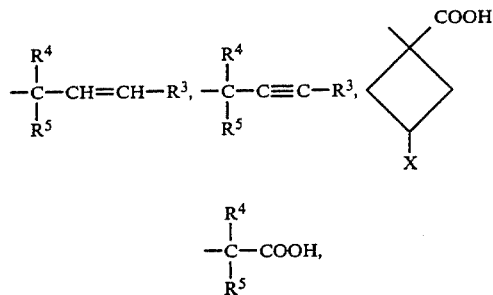

in which $R^3$ is hydrogen, (lower)alkyl or carboxyl, X is halogen, hydroxy or (lower)alkoxy, and $R^4$ and $R^5$ are each independently hydrogen, methyl or ethyl, or $R^4$ and $R^5$, taken together with the carbon atom to which they are attached, may be a cycloalkylidene ring containing from 3 to 5 carbon atoms, and

is a quaternary ammonio group, or a nontoxic pharmaceutically acceptable salt, physiologically hydrolyzable ester or solvate thereof.

2. A compound of claim 1 wherein

is

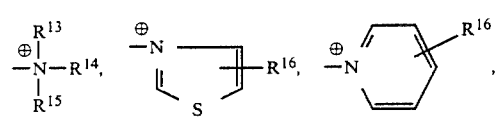

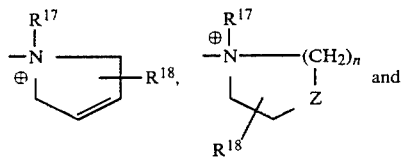

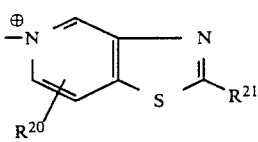

wherein $R^{13}$, $R^{14}$ and $R^{15}$ are the same or different and are (lower)alkyl, (lower)alkenyl, amino(lower)alkyl with the provision that the amino may not be on an α-carbon, or hydroxy(lower)alkyl with the provision that the hydroxy group may not be on an α-carbon;

$R^{16}$ is hydrogen, (lower)alkyl, (lower)alkoxy, (lower)alkylthio, amino, (lower)alkylamino, di(lower)alkylamino, formylamino, (lower)alkanoylamino, hydroxy, hydroxy(lower)alkyl, halo(lower)alkyl, amino(lower)alkyl, (lower)alkoxy(lower)alkyl or carbamoyl;

$R^{17}$ is (lower)alkyl, (lower)alkoxy(lower)alkyl, halo(lower)alkyl, allyl, hydroxy(lower)alkyl with the provision that the hydroxy group is not on the α-carbon, amino(lower)alkyl with the provision that the amino group is not on the α-carbon, or phenyl(lower)alkyl;

$R^{18}$ is hydrogen, (lower)alkyl, (lower)alkoxy, (lower)alkoxy(lower)alkyl, (lower)alkylthio, amino, (lower)alkylamino, di(lower)alkylamino, hydroxy, hydroxy(lower)alkyl, amino(lower)alkyl, formylamino, (lower)alkanoylamino or carbamoyl;

n is an integer of from 1 to 3, inclusive;

Z is $CH_2$ or, when n is 2, Z also may be S, O or $N-R^{19}$, in which $R^{19}$ is hydrogen or (lower)alkyl; and $R^{20}$ and $R^{21}$ are the same or different and are hydrogen, (lower)alkyl, (lower)alkoxy, (lower)alkylthio, amino, (lower)alkylamino, di(lower)alkylamino, hydroxy, hydroxy(lower)alkyl, amino(lower)alkyl, (lower)alkoxy(lower)alkyl, carboxy(lower)alkyl, carboxy(lower)alkylamino, (lower)alkanoylamino, carboxy(lower)alkanoylamino or carbamoyl.

3. A compound of claim 1 in which

is

in which $R^{13}$, $R^{14}$ and $R^{15}$ are the same or different and are (lower)alkyl.

4. A compound of claim 1 in which

is

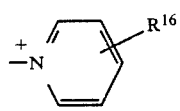

in which $R^{16}$ is hydrogen, amino or carbamoyl.

5. A compound of claim 1 wherein

is

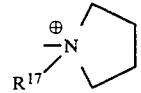

in which $R^{17}$ is (lower)alkyl.

6. A compound of claim 1 wherein

is

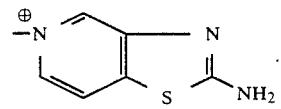

7. A compound of claim 1 wherein is

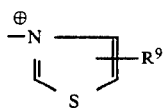

in which R⁹ is (lower)alkyl or (lower)alkylthio.

8. A compound of claim 1 wherein

is

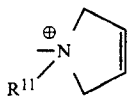

in which R¹¹ is (lower)alkyl.

9. The compound of claim 1 which is 7-[(Z)-2-(2-aminothiazol-4-yl)-2-methoxyiminoacetamido]-3-[3-(1-methylpyrrolidinio)-1-propen-1-yl]-3-cephem-4-carboxylate, or a nontoxic pharmaceutically acceptable salt, physiologically hydrolyzable ester or solvate thereof.

10. The compound of claim 1 which is 7-[(Z)-2-(2-aminothiazol-4-yl)-2-methoxyiminoacetamido]-3-(3-pyridinio-1-propen-1-yl)-3-cephem-4-carboxylate, or a nontoxic pharmaceutically acceptable salt, physiologically hydrolyzable ester or solvate thereof.

11. The compound of claim 1 which is 7-[(Z)-2-(2-aminothiazol-4-yl)-2-(2-carboxy-2-propoxyimino)acetamido]-3-(3-pyridinio-1-propen-1-yl)-3-cephem-4-carboxylate, or a nontoxic pharmaceutically acceptable salt, physiologically hydrolyzable ester or solvate thereof.

12. The compound of claim 1 which is 7-[(Z)-2-(2-aminothiazol-4-yl)-2-(1-carboxycyclobut-1-oxyimino)acetamido]-3-[3-(1-methylpyrrolidinio)-1-propen-1-yl]-3-cephem-4-carboxylate, or a nontoxic pharmaceutically acceptable salt, physiologically hydrolyzable ester or solvate thereof.

13. The compound of claim 1 which is 7-[(Z)-2-(2-aminothiazol-4-yl)-2-(1-carboxycyclobut-1-oxyimino)acetamido]-3-(3-pyridino-1-propen-1-yl)-3-cephem-4-carboxylate, or a nontoxic pharmaceutically acceptable salt, physiologically hydrolyzable ester or solvate thereof.

14. The compound of claim 1 which is 7-[(Z)-2-(2-aminothiazol-4-yl)-2-(1-carboxycyclobut-1-oxyimino)acetamido]-3-[3-(2-amino-5-thiazolo[4,5-c]pyridinio)-1-propen-1-yl]-3-cephem-4-carboxylate, or a nontoxic pharmaceutically acceptable salt, physiologically hydrolyzable ester or solvate thereof.

15. The compound of claim 1 which is 7-[(Z)-2-(2-aminothiazol-4-yl)-2-methoxyiminoacetamido]-3-[3-(trimethylammonio)-1-propen-1-yl]-3-cephem-4-carboxylate, or a nontoxic pharmaceutically acceptable salt, physiologically hydrolyzable ester or solvate thereof.

16. The compound of claim 1 which is 7-[(Z)-2-(2-aminothiazol-4-yl)-2-methoxyiminoacetamido]-3-[3-(3-aminopyridinio)-1-propen-1-yl]-3-cephem-4-carboxylate, or a nontoxic pharmaceutically acceptable salt, physiologically hydrolyzable ester or solvate thereof.

17. The compound of claim 1 which is 7-[(Z)-2-(2-aminothiazol-4-yl)-2-methoxyiminoacetamido]-3-[3-(1-methyl-3-pyrroliino)-1-propen-1-yl]-3-cephem-4-carboxylate, or a nontoxic pharmaceutically acceptable salt, physiologically hydrolyzable ester or solvate thereof.

18. The compound of claim 1 which is 7-[(Z)-2-(2-aminothiazol-4-yl)-2-(1-carboxycyclobut-1-oxyimino)acetamido]-3-[3-(1-methyl-3-pyrrolinio)-1-propen-1-yl]-3-cephem-4-carboxylate, or a nontoxic pharmaceutically acceptable salt, physiologically hydrolyzable ester or solvate thereof.

19. The compound of claim 1 which is 7-[(Z)-2-(2-aminothiazol-4-yl)-2-(2-carboxy-2-propoxyimino)acetamido]-3-[3-(1-methylpyrrolidinio)-1-propen-1-yl]-3-cephem-4-carboxylate, or a nontoxic pharmaceutically acceptable salt, physiologically hydrolyzable ester or solvate thereof.

20. The compound of claim 1 which is 7-[(Z)-2-(2-aminothiazol-4-yl)-2-(1-carboxycyclobut-1-oxyimino)acetamido]-3-[3-(2-methylthio-3-thiazolio)-1-propen-1-yl]-3-cephem-4-carboxylate, or a nontoxic pharmaceutically acceptable salt, physiologically hydrolyzable ester or solvate thereof.

21. The compound of claim 1 which is 7-[(Z)-2-(2-aminothiazol-4-yl)-2-methoxyiminoacetamido]-3-[3-(2-methyl-3-thiazolio)-1-propen-1-yl]-3-cephem-4-carboxylate, or a nontoxic pharmaceutically acceptable salt, physiologically hydrolyzable ester or solvate thereof.

22. The compound of claim 1 which is 7-[(Z)-2-(2-aminothiazol-4-yl)-2-(2-carboxy-2-propoxyimino)acetamido]-3-[3-(2-methylthio-3-thiazolio)-1-propen-1-yl]-3-cephem-4-carboxylate, or a nontoxic pharmaceutically acceptable salt, physiologically hydrolyzable ester or solvate thereof.

23. The compound of claim 1 which is 7-[(Z)-2-(2-aminothiazol-4-yl)-2-(1-carboxycyclobut-1-oxyimino)acetamido]-3-[3-(4-aminopyridino)-1-propen-1-yl]-3-cephem-4-carboxylate, or a nontoxic pharmaceutically acceptable salt, physiologically hydrolyzable ester or solvate thereof.

24. The compound of claim 1 which is 7-[(Z)-2-(2-aminothiazol-4-yl)-2-methoxyiminoacetamido]-3-[3-(4-amino-1-pyridinio)-1-propen-1-yl]-3-cephem-4-carboxylate, or a nontoxic pharmaceutically acceptable salt, physiologically hydrolyzable ester or solvate thereof.

25. The compound of claim 1 which is 7-[(Z)-2-(2-aminothiazol-4-yl)-2-methoxyiminoacetamido]-3-[3-(2-methylthio-3-thiazolio)-1-propen-1-yl]-3-cephem-4-carboxylate, or a nontoxic pharmaceutically acceptable salt, physiologically hydrolyzable ester or solvate thereof.

26. The compound of claim 1 which is 7-[(Z)-2-(2-aminothiazol-4-yl)-2-(1-carboxycyclobut-1-oxyimino)acetamido]-3-[3-(3-amino-1-pyridinio)-1-propen-1-yl]-3-cephem-4-carboxylate, or a nontoxic pharmaceutically acceptable salt, physiologically hydrolyzable ester or solvate thereof.

27. The compound of claim 1 which is 7-[(Z)-2-(2-aminothiazol-4-yl)-2-methoxyiminoacetamido]-3-[3-(4-carbamoyl-1-pyridinio)-1-propen-1-yl]-3-cephem-4-carboxylate, or a nontoxic pharmaceutically acceptable salt, physiologically hydrolyzable ester or solvate thereof.

28. The compound of claim 1 which is 7-[(Z)-2-(2-aminothiazol-4-yl)-2-methoxyiminoacetamido]-3-[3-(2-amino-5-thiazolo[4,5-c]pyridinio)-1-propen-1-yl]-3-cephem-4-carboxylate, or a nontoxic pharmaceutically acceptable salt, physiologically hydrolyzable ester or solvate thereof.

29. The compound of claim 1 which is 7-[(Z)-2-(2-aminothiazol-4-yl)-2-(1-carboxycyclobut-1-oxyimino)acetamido]-3-[3-(2-methyl-3-thiazolio)-1-propen-1-yl]-3-cephem-4-carboxylate, or a nontoxic pharmaceutically acceptable salt, physiologically hydrolyzable ester or solvate thereof.

* * * * *

UNITED STATES PATENT AND TRADEMARK OFFICE
CERTIFICATE OF CORRECTION

PATENT NO. : 4,486,586
DATED : December 4, 1984
INVENTOR(S) : Yukio Narita et al.

It is certified that error appears in the above—identified patent and that said Letters Patent is hereby corrected as shown below:

In Column 14, the structure and text shown as

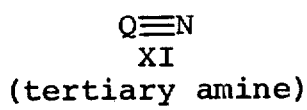

(tertiary amine)

should be shown as

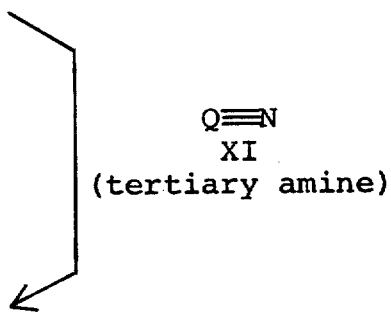

with the bent arrow running from structure X to structure XII.

The last structure in Column 17 should read as follows.

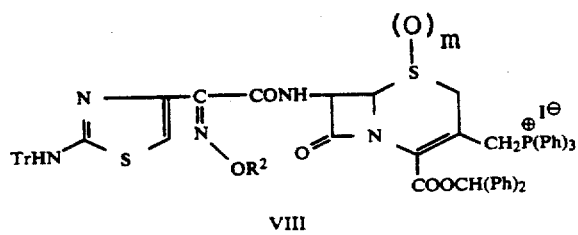

VIII

UNITED STATES PATENT AND TRADEMARK OFFICE
CERTIFICATE OF CORRECTION

PATENT NO. : 4,486,586

DATED : December 4, 1984

INVENTOR(S) : Yukio Narita et al.

It is certified that error appears in the above—identified patent and that said Letters Patent is hereby corrected as shown below:

The first structure in Column 21 should read as follows:

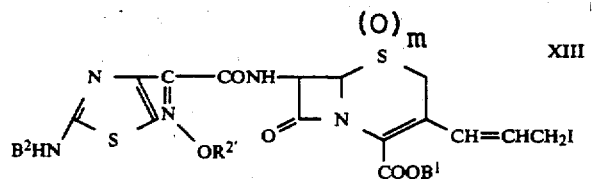

The structure at Line 40 of Column 25 should read as follows:

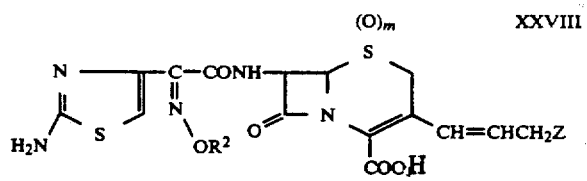

The structure and text at Lines 10-12 of Column 43 should read as follows:

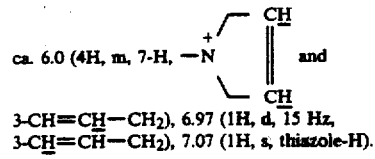

3-CH=CH—CH$_2$), 6.97 (1H, d, 15 Hz, 3-CH=CH—CH$_2$), 7.07 (1H, s, thiazole-H).

The structure and text at Lines 5-7 of Column 46 should read as follows:

UNITED STATES PATENT AND TRADEMARK OFFICE
CERTIFICATE OF CORRECTION

PATENT NO. : 4,486,586
DATED : December 4, 1984
INVENTOR(S) : Yukio Narita et al.

It is certified that error appears in the above—identified patent and that said Letters Patent is hereby corrected as shown below:

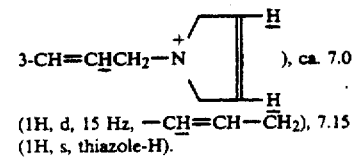

(1H, d, 15 Hz, —CH=CH—CH$_2$), 7.15
(1H, s, thiazole-H).

The structure at Column 48, Line 39, should read as follows:

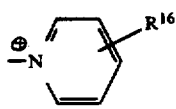

In Column 50, Line 5, "-3-pyrroliino)-" should read -- 3-pyrrolinio) -- .

Signed and Sealed this

Eleventh Day of June 1985

[SEAL]

Attest:

DONALD J. QUIGG

Attesting Officer

Acting Commissioner of Patents and Trademarks